United States Patent
Coburn et al.

(10) Patent No.: US 7,291,620 B2
(45) Date of Patent: Nov. 6, 2007

(54) N-ALKYL PHENYLCARBOXAMIDE BETA-SECRETASE INHIBITORS FOR THE TREATMENT OF ALZHEIMER'S DISEASE

(75) Inventors: Craig A. Coburn, Royersford, PA (US); Shawn J. Stachel, Perkasie, PA (US); Joseph P. Vacca, Telford, PA (US); Harold G. Selnick, Ambler, PA (US)

(73) Assignee: Merck + Co., Inc., Rahway, NJ (US)

( * ) Notice: Subject to any disclaimer, the term of this patent is extended or adjusted under 35 U.S.C. 154(b) by 0 days.

(21) Appl. No.: 10/563,538

(22) PCT Filed: Jun. 25, 2004

(86) PCT No.: PCT/US2004/020234

§ 371 (c)(1),
(2), (4) Date: Dec. 19, 2005

(87) PCT Pub. No.: WO2005/004802

PCT Pub. Date: Jan. 20, 2005

(65) Prior Publication Data

US 2006/0161020 A1    Jul. 20, 2006

Related U.S. Application Data

(60) Provisional application No. 60/483,992, filed on Jun. 30, 2003.

(51) Int. Cl.
*A61K 31/4965* (2006.01)
*A61K 31/445* (2006.01)
*A61K 31/40* (2006.01)
*A61K 31/279* (2006.01)
*A61K 31/16* (2006.01)

(52) U.S. Cl. ............... 514/255.01; 514/330; 514/423; 514/424; 514/522; 514/600; 514/605; 514/616; 544/391; 544/226; 548/538; 548/550; 558/413; 564/79; 564/99; 564/153

(58) Field of Classification Search ........... 514/255.01, 514/330, 423, 424, 522, 600, 605, 616; 544/391, 544/226; 548/538, 550; 558/413; 564/79, 564/99, 153
See application file for complete search history.

(56) References Cited

U.S. PATENT DOCUMENTS 6,962,934 B2 * 11/2005 Warpehoski et al. ........ 514/354

FOREIGN PATENT DOCUMENTS

| WO | WO89/04833 | 6/1989 |
| WO | WO 01/00665 | 1/2001 |
| WO | WO 02/02506 | 1/2002 |
| WO | WO 03/043975 | 5/2003 |
| WO | WO 03/057721 | 7/2003 |
| WO | WO 2004/043916 | 5/2004 |

OTHER PUBLICATIONS

C. A. Coburn et al., "Identification of a Small Molecule Nonpeptide Active Site Beta-Secretase Inhibitor That Displays a Nontraditional Binding Mode for Aspartyl Proteases," J. Med. Chemistry, vol. 47, pp. 6117-6119 (2004).

* cited by examiner

*Primary Examiner*—Peter O'Sullivan
(74) *Attorney, Agent, or Firm*—William Krovatin; John C. Todaro

(57) ABSTRACT

The present invention is directed to compounds which are inhibitors of the beta-secretase enzyme and which are useful in the treatment or prevention of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

12 Claims, No Drawings

N-ALKYL PHENYLCARBOXAMIDE BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) from Provisional Application No. 60/483,992, filed Jun. 30, 2003.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase, which cleaves near the $NH_2$-terminus of Aβ and produces COOH-terminal fragments (CTFs) which contain the whole Aβ domain.

Thus, the activity of β-secretase, or β-site amyloid precursor protein-cleaving enzyme ("BACE"), leads to the abnormal cleavage of APP, production Aβ, and accumulation of β amyloid plaques in the brain, which is a characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of the β-secretase or BACE, thus preventing the formation of insoluble Aβ and arresting the production of Aβ.

SUMMARY OF THE INVENTION

The present invention is directed to compounds that are inhibitors of the β-secretase enzyme and BACE and which are useful in the treatment of diseases in which the β-secretase enzyme is involved, such as Alzheimer's disease. The invention is also directed to pharmaceutical compositions comprising these compounds and the use of these compounds and compositions in the prevention or treatment of such diseases in which the β-secretase enzyme is involved.

DETAILED DESCRIPTION OF THE INVENTION

The present invention is directed to compounds of the formula I:

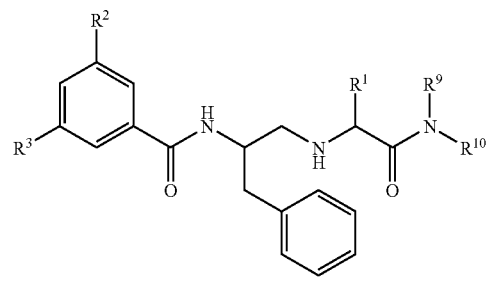

wherein:
$R^1$ is selected from the group consisting of:
  (1) $C_{1-6}$alkyl, unsubstituted or substituted with —$OR^5$ or —$S(O)_2$—$C_{1-6}$alkyl,
  (2) hydrogen,
  (3) phenyl, and
  (4) benzyl;
$R^2$ is selected from the group consisting of:
  (1) hydrogen,
  (2) $R^4$—$S(O)_p$—,
     wherein $R^4$ is independently selected from the group consisting of:
       (a) $C_{1-6}$alkyl, which is unsubstituted or substituted with 1-6 fluoro,
       (b) phenyl, and
       (c) benzyl,
  (3) $R^4$—$S(O)_pN(R^5)$—,
     wherein $R^5$ is independently selected from the group consisting of:
       (a) hydrogen,
       (b) —$C_{1-6}$alkyl, which is unsubstituted or substituted with 1-6 fluoro,
       (c) —$C_{3-6}$cycloalkyl which is unsubstituted or substituted with methyl,
       (d) phenyl, which is unsubstitued or substituted with halo or methoxy, and
       (e) benzyl,
  (4) —CN,
  (5) —$C_{1-6}$alkyl-CN,
  (6) halogen,
  (7)

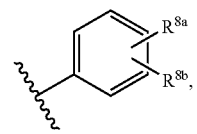

wherein $R^{8a}$ and $R^{8b}$ are independently selected from the group consisting of:
  (a) hydrogen,
  (b) —CN,
  (c) halo,
  (d) —$C_{1-6}$alkyl,
  (e) —O—$R^5$, (f) —S—R$^5$,
(g) —CO$_2$R$^5$, and
(h) tetrazolyl, (8)

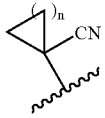

wherein n is 1, 2, 3 or 4;
R$^3$ is selected from the group consisting of:

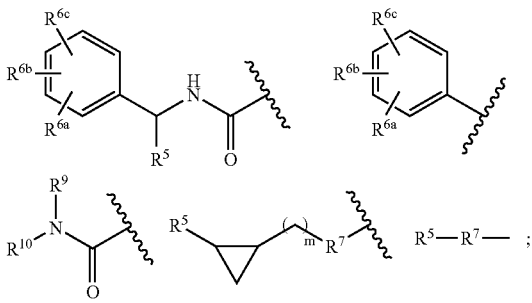

R$^{6a}$, R$^{6b}$, and R$^{6c}$ are independently selected from the group consisting of:
(1) hydrogen,
(2) halogen,
(3) —OR$^5$,
(4) —SR$^5$, and
(5) —C$_{1-6}$alkyl;
R$^7$ is selected from the group consisting of a bond, —CH═CH—, —O—, —S—, and —NH—;
R$^9$ and R$^{10}$ are independently selected from the group consisting of:
(1) hydrogen,
(2) C$_{1-6}$alkyl, unsubstituted or substituted with —CN or 1-4 halo,
(3) —C$_{3-6}$cycloalkyl,
(4) phenyl, which is unsubstitued or substituted with halo or methoxy, and
(5) benzyl,
or R$^9$ and R$^{10}$ may be joined together to form a pyrrolidine or piperidine ring which is unsubstituted or substituted with benzyl, —OR$^5$ or 1-4 halo;
m is independently 0, 1, or 2;
p is independently 0, 1, or 2, and pharmaceutically acceptable salts thereof.

An embodiment of the present invention includes compounds wherein R$^1$ is C$_{1-6}$alkyl.

Another embodiment of the present invention includes compounds wherein R$^1$ is methyl.

Another embodiment of the present invention includes compounds wherein R$^1$ is ethyl.

Another embodiment of the present invention includes compounds wherein R$^2$ is:

R$^4$—S(O)$_2$—NR$^5$— and wherein R$^4$ is selected from the group consisting of:
(1) C$_{1-6}$alkyl,
(2) phenyl, and
(3) benzyl;
R$^5$ is selected from the group consisting of:
(1) C$_{1-6}$alkyl,
(2) phenyl,
(3) benzyl, and
(4) hydrogen.

Another embodiment of the present invention includes compounds wherein R$^3$ is:

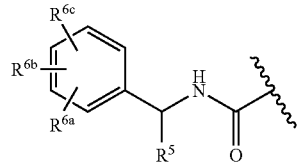

and wherein R$^5$ is methyl, R$^{6a}$ is H or F, R$^{6b}$ and R$^{6c}$ are hydrogen.

Another embodiment of the present invention includes compounds wherein R$^3$ is:

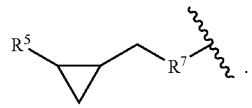

Another embodiment of the present invention includes compounds wherein R$^9$ is hydrogen.

Another embodiment of the present invention includes compounds wherein R$^{10}$ is C$_{1-6}$alkyl.

Another embodiment of the present invention includes compounds wherein R$^{10}$ is iso-butyl.

Another embodiment of the present invention includes a compound which is selected from the title compounds of the following Examples and pharmaceutically acceptable salts thereof.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Scheme 1.

amine base to afford an N-protected amino amide (1—B). The Boc group is removed under acidic conditions such as HCl gas in ethyl acetate. The resulting amino acid amide salt (1—C) is reductively aminated with boc protected phenylalanine aldehyde using a reducing agent such as sodium cyanoborohydride in methanol. The product (1-D) is treated with a strong acid such as HCl gas or trifluoroacetic acid to remove the t-butyloxycarbonyl protecting group to provide the intermediate diamine salt (1-E). Compounds 1-E are coupled to benzoic acid derivatives by standard amide coupling procedures such as BOP reagent and a trialkylamine base to provide final compounds (I).

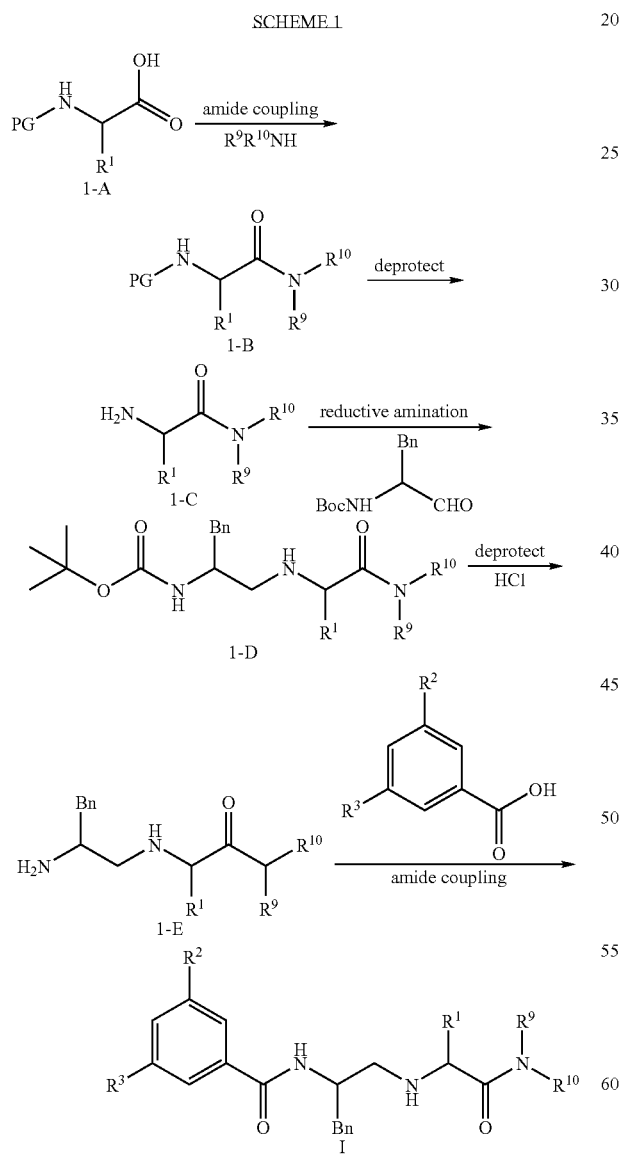

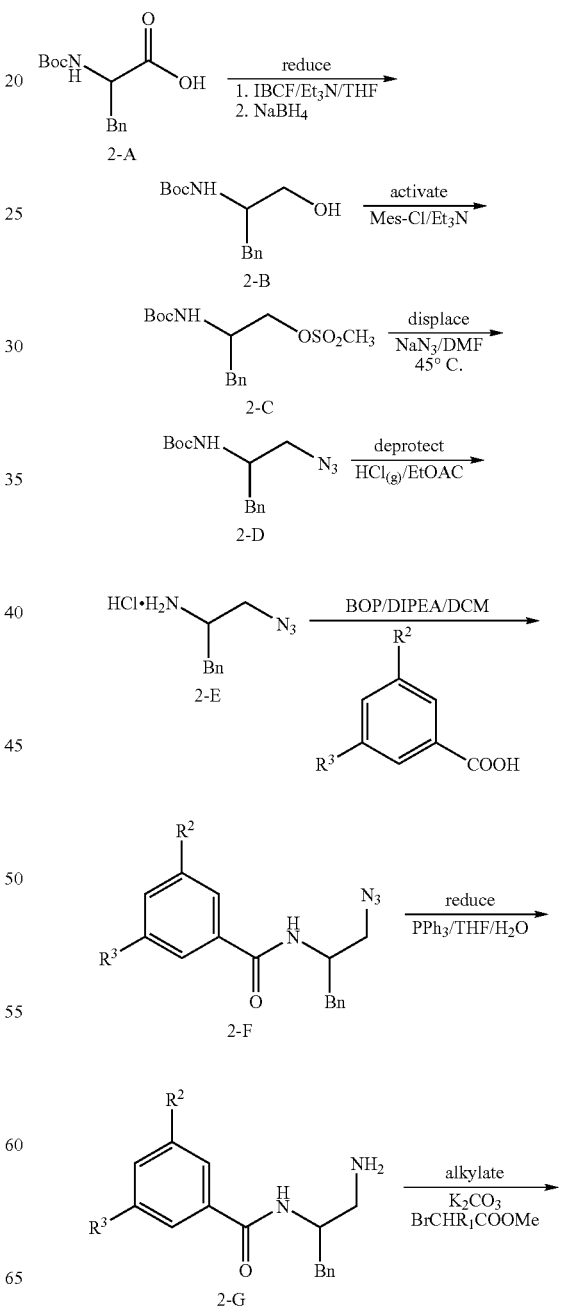

Referring to Scheme 1, N-Boc protected amino acids (1—A) are reacted with primary or secondary amines in the presence of a coupling agent such as BOP reagent and an

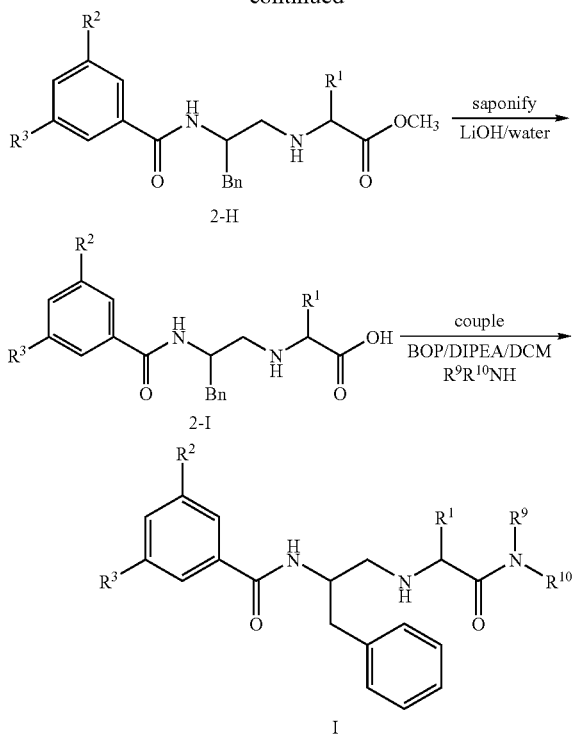

Scheme 2 illustrates an alternative process for the synthesis of inhibitors (I). Boc-Phe is reduced by standard methods to afford the corresponding alcohol (2-B). The resulting alcohol is activated for azide displacement by treatment with methanesulfonyl chloride and an amine base such as triethylamine. Azide formation takes place by reacting mesylate 2-C with an excess of sodium azide in a polar aprotic solvent such as DMF at an elevated temperature. The product (2-D) is treated with a strong acid such as HCl gas to remove the t-butyloxycarbonyl protecting group to provide the amino azide salt 2-E. Standard amide coupling of amine 2-E with a benzoic acid derivative provides 2-F. The azide functional group is reduced with a phosphine reagent to provide 2-G which is then alkylated with an appropriately substituted bromoacetate ester and a base such as potassium carbonate. The ester 2-H is then saponified with a base such as lithium hydroxide to afford the corresponding carboxylic acid. Compounds 2-I are coupled to a benzoic acid derivative by standard amide coupling procedures such as BOP reagent and a trialkylamine base to provide final compounds I.

A wide variety of benzoic acids are applicable to schemes 1 and 2 and include examples where $R^2$ is sulfonamide, sulfone, amide, nitrile, alkylnitrile, halogen, phenyl, and cyanocycloalkyl. $R^3$ of the benzoic acid in Schemes 1 and 2 is generally selected from a carboxyaminobenzyl group, a substituted olefin, an O or N alkylcyclopropyl, or an alkyl ether, alkylthioether, or secondary amine.

The term "substantially pure" means that the isolated material is at least 90% pure, and preferably 95% pure, and even more preferably 99% pure as assayed by analytical techniques known in the art. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, preventing, ameliorating, controlling or reducing the risk of Alzheimer's disease, other diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil and tacrine; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, granulating and disintegrating agents, binding agents and lubricating agents. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent or as soft gelatin capsules wherein the active ingredient is mixed with water or an oil medium.

Aqueous suspensions contain the active materials in admixture with excipients suitable for the manufacture of aqueous suspensions. Such excipients include suspending agents and dispersing or wetting agents. The aqueous suspensions may also contain one or more preservatives, coloring agents, flavoring agents, and sweetening agents.

Oily suspensions may be formulated by suspending the active ingredient in a vegetable oil or in a mineral oil. The oily suspensions may contain a thickening agent. Sweetening agents and flavoring agents may be added to provide a palatable oral preparation. These compositions may be preserved by the addition of an anti-oxidant.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, may also be present.

The pharmaceutical compositions of the invention may also be in the form of oil-in-water emulsions, which may also contain excipients such as sweetening and flavoring agents.

The pharmaceutical compositions may also be in the form of a sterile injectable aqueous or oleagenous suspension, which may be formulated according to the known art, or may be administered in the form of suppositories for rectal administration of the drug.

The compounds of the present invention may also be administered by inhalation, by way of inhalation devices known to those skilled in the art, or transdermally by way of transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology or the diseased (i.e., reversing the pathology and/or symptomatology). The term "controlling" includes preventing, treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person adminstering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person adminstering the drug to the patient. Such kits may be provided with all necessary materials and ingredients contained therein, or they may contain instructions for using or making materials or components that must be obtained independently by the patient or person administering the drug to the patient.

When treating, preventing, controlling, ameliorating, or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 milligrams to about 2000 milligrams, preferably from about 0.1 milligrams to about 20 milligrams per kilogram of body weight. In the case of a 70 kg adult human, the total daily dose will generally be from about 7 milligrams to about 1,400 milligrams. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient, more preferably comprising about 0.5 mg to 500 mg active ingredient or 0.5 mg to 250 mg active ingredient, or 1 mg to 100 mg active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The $K_m$ of the substrate is not determined due to the limit of solubility of the substrate. A typical reaction contains approximately 30 nM enzyme, 1.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 μM, 10 μM, 1 μM) were included in the reactions mixture (final DMSO concentration is 0.8%). All experiments were conducted at room temperature using the standard reaction conditions described above. To determine the $IC_{50}$ of the compound, competitive equation $V0/Vi=1+[I]/[IC50]$ was used to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The $K_m$ of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 1 µM. Such a result is indicative of the intrinsic activity of the compounds in use as inhibitors the beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way.

Intermediate I

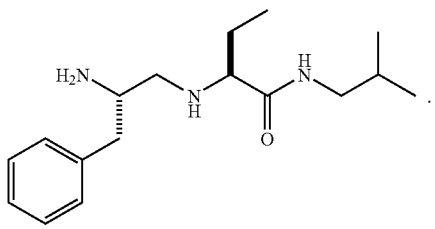

Step A: To a solution containing 2.0 g (10.0 mmol) of (S)—N-Boc-aminobutyric acid in 50 mL of DCM was added 730 mg (10.0 mmol) of isobutyl amine, 4.42 g (10.0 mmol) of BOP Reagent and 4.2 mL (24.0 mmol) of Hunig's base. The reaction mixture was stirred at rt for 30 min before it was extracted with 10% citric acid (10 mL), water (10 mL), saturated NaHCO$_3$ (10 mL) and brine (10 mL). The organic phase was dried over MgSO$_4$, concentrated and chromatographed (1:1 EtOAc/Hexanes) to afford 2.4 g of the desired amide. $^1$H NMR δ 6.11 (bs, 1H), 4.96 (bs, 1H), 3.97 (m, 1H), 3.08 (m, 2H), 1.88 (m, 1H), 1.80 (m, 1H), 1.66 (m, 1H), 1.45 (s, 9H), 0.95 (m, 9H). LCMS (M+H)=259.27

Step B: A 0° C. solution containing 1.58 g (6.10 mmol) of Boc amide A was dissolved in 40 mL of EtOAc and 4 ml of MeOH and saturated with HCl gas for 10 minutes. The reaction mixture was stirred for 1 h then concentrated to a semi-solid. The residue was triturated with 50 mL of ether to afford 1.10 g of the amine HCl salt as an extremely hygroscopic solid. $^1$H NMR (CD$^3$OD) δ 3.78 (t, J=7.8 Hz, 1H), 3.18 (m, 2H), 1.85 (m, 3H), 1.01 (t, J=7.8 Hz, 3H), 0.87 (d, 6H). LCMS (M+H)=159.31

Step C: To a solution containing 200 mg (0.76 mmol) of (S)—N-Boc-Phe-CHO in 5 mL of MeOH was added 746 mg (3.81 mmol, 5 equiv) of amine B and 47.0 mg (0.76 mmol) of NaBH$_3$CN. The resulting solution was stirred at rt over 16 h. The solvent was removed and the residue was dissolved in 25 mL of DCM and washed with NaHCO$_3$ (10 mL) and brine (10 mL). Evaporation of the solvent and chromatography (EtOAc) left 245 mg of the desired product that was used directly in the next reaction. $^1$H NMR (CDCl$_3$) δ 7.4-7.1 (m, 5H), 4.84 (d, J=2.4 Hz, 1H), 4.11 (bs, 1H), 3.60 (bs, 1H), 3.11 (m, 4H), 2.82 (m, 4H), 1.81 (m, 4H), 1.43 (s, 9H), 0.99 (t, J=7.8 Hz, 3H), 0.82 (d, J=7.7 Hz, 6H).

Step D: A 0° C. solution containing 201 mg (0.5 mmol) of Boc amine from step C was dissolved in 25 mL of EtOAc and saturated with HCl gas for 5 minutes. The reaction mixture was stirred for 1 h, concentrated and triturated with ether to afford 185 mg of compound I as a white solid. $^1$H NMR (CD3OD) δ 7.44-7.15 (m, 5H), 3.83 (m, 1H), 3.33 (m, 1H), 3.18 (m, 1H), 3.06 (m, 4H), 2.00 (m, 2H), 1.77 (m, 1H), 1.01 (t, J=7.8 Hz, 3H), 0.88 (d, J=7.8 Hz, 6H).

Intermediate II

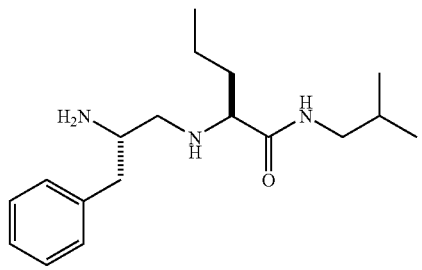

Prepared similar to Intermediate I but substituting (S)—N-Boc-aminopentanoic acid as the amine in step A. $^1$H NMR (CD$_3$OD) δ 8.55 (bt, 1H), 7.41-7.26 (m, 5H), 3.92 (t, J=6.8 Hz, 2H), 3.77 (dd, 2H), 3.30 (d, J=1.7 Hz, 1H), 3.08 (dd, J=13.5, 1.7 Hz, 1H), 3.03-2.95 (m, 4H), 1.88 (m, 2H), 1.77 (m, 1H), 1.41 (m, 2H), 0.94 (t, J=7.4 Hz, 3H), 0.90 (d, J=6.8 Hz, 6H)

Intermediate III

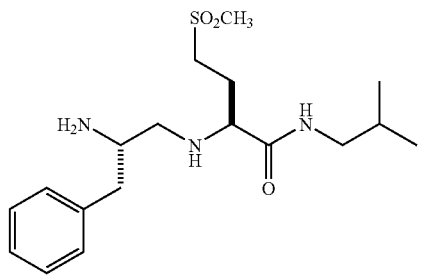

Prepared similar to Intermediate I but substituting (S)—N-Boc-methionine sulfone as the amine in step A. $^1$H NMR (CD$_3$OD) δ 8.42 (bs, 1H), 7.44-7.25 (m, 5H), 4.02 (m, 1H), 3.83 (m, 1H), 3.38-3.05 (m, 7H), 3.00 (s, 3H), 2.39 (bd, 2H), 1.77 (m, 1H), 0.92 (d, J=6.7 Hz, 6H).

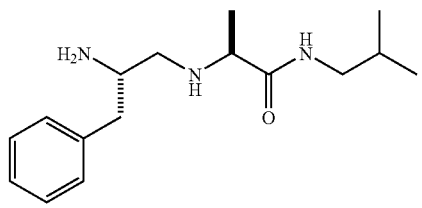

Intermediate IV

Prepared similar to Intermediate I but substituting (S)—N-Boc-alanine as the amine in step A. $^1$H NMR (CD$_3$OD) δ 8.41 (bt, 1H), 7.41-7.26 (m, 5H), 4.02 (m, 1H), 3.81 (m, 2H), 3.40-3.00 (m, 5H), 1.80 (m, 2H), 1.61 (d, J=6.7 Hz, 3H), 0.97 (d, J=6.8 Hz, 6H)

Intermediate V

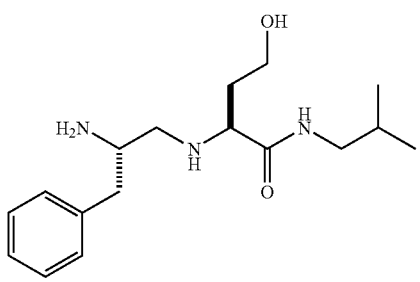

Prepared similar to Intermediate I but substituting (S)—N-Boc-homoserine as the amine in step A. ¹H NMR (CD₃OD):. δ 7.37-7.27 (m, 5H), 4.13 (m, 1H), 3.99 (m, 1H), 3.86-3.75 (m, 2H), 3.38-3.25 (m, 2H), 3.03 (m, 2H), 2.89 (m, 1H), 2.76 (d, J=7.14 Hz, 2H), 2.14 (m, 1H), 1.99 (m, 1H), 1.01 (d, J=6.68 Hz, 6H). LCMS (M+H)=308.1

EXAMPLE 1

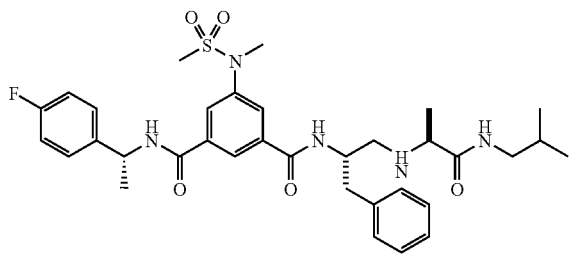

Step A. To a stirred slurry of dimethyl 5-aminoisophthalate (5.0 g, 23.90 mmol) in 100 mL CH₂Cl₂/Pyridine (3:1) at 0° C. was added methanesulfonyl chloride (1.85 mL, 23.90 mmol). The resulting mixture was stirred for 4 h at room temperature. The solvent was removed in vacuo and ethyl acetate (100 mL) was added resulting in precipitate formation. The product was collected by filtration to give 5.14 g of the sulfonamide as a white solid. ¹H NMR (DMSO_d6) δ 8.15 (s, 1H), 8.02 (s, 2H), 3.89 (s, 6H), 3.02 (s, 3H). LCMS [M−OCH₃]⁺=256.16

Step B. To a solution of sodium hydride (0153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H₂O (100 mL) and extracted with EtOAc (3×50 mL). The organic extracts were dried over MgSO₄ and evaporated to give 1.03 g of N-methylsulfonamide. ¹H NMR (DMSO_d6) δ 8.40 (s, 1H), 8.19 (s, 2H), 3.91 (s, 6H), 3.34 (s, 3H), 3.01 (s, 3H). LCMS [M+H]=302.15

Step C. Diester (1.03 g, 3.38 mmol) from step B was dissolved in 50 mL THF: MeOH (1:1) and cooled to 0° C. 1N NaOH (3.38 mL, 3.38 mmol) was added and the reaction was allowed to warm to RT over 8 hours. The solution was acidified with 1N HCl (30 mL) and extracted with EtOAc (3×50 mL). The combined organic extracts were washed with brine and dried over MgSO₄, filtered and concentrated in vacuo. Purification on silica gel (5% MeOH/CHCl₃ containing 1% HOAc) gave 795 mg (82%) of the mono acid. ¹H NMR (DMSO_d6) δ 8.30 (s, 1H), 8.10 (s, 2H), 3.84 (s, 3H), 3.27 (s, 3H), 2.94 (s, 3H). LCMS (M+H)=288.16

Step D. A solution containing 133 mg (0.46 mmol) of the monoacid from step C in 5 mL CH₂Cl₂, BOP reagent (0.235 g, 0.55 mmol), (R)— (+)-4-fluoro-methylbenzylamine (76 mg, 0.55 mmol), and diisopropylethylamine (0.24 mL, 1.39 mmol) was stirred at ambient temperature for 1 h. Evaporation of the solvent and column chromatography on silica gel (90% EtOAc/Hexanes) afforded 71 mg of the benzyl amide. LCMS (M+H)=409.27

Step E. To 179 mg (0.438 mmol) of the benzyl amide from step D in 10 mL THF:MeOH (1:1) was added 2 N NaOH (0.66 mL, 1.32 mmol). The solution was heated to 50° C. for 1 h. After cooling the solution was acidified by the addition of 1 N HCl (20 mL) and extracted with EtOAc (3×30 mL). The combined organic extracts were dried over MgSO₄, filtered, and concentrated in vacuo to yield 173 g of the desired carboxylic acid. ¹H NMR (CDCl₃) δ 8.22 (t, 1H), 8.11 (m, 1H), 8.06 (m, 1H), 7.34 (m, 5H), 6.47 (d, J=7.1 Hz, 1H), 5.33 (m, 1H), 3.37 (s, 3H), 2.87 (s, 3H), 1.64 (d, J=7.0 Hz, 3H). LCMS (M+H)=395.2

Step F. To a solution containing 39.5 mg (0.10 mmol) of the carboxylic acid from step E in 5 mL of DCM was added intermediate amine dihydrochloride IV (35.7 mg, 0.10 mmol), 44.2 mg (0.10 mmol) of BOP reagent and 0.076 mL (0.44 mmol) of diisopropylethyl amine. The reaction mixture was stirred at rt for 1 h then extracted with 2×1 mL 1N HCl, 2×1 mL water, and 1 mL brine. The organic phase was dried over MgSO₄ and subjected to reverse phase chromatography to afford 57.7 mg of the desired product as a white solid. 1H NMR (CD₃OD) δ 9.03 (d, J=7.69 Hz, 1H), 8.90 (bs, 1H), 8.61 (d, J=8.42 Hz, 1H), 8.45 (m, 1H), 8.23 (s, 1H), 8.03 (s, 1H), 7.92 (s, 1H), 7.44 (m, 2H), 7.29-7.14 (m, 7H), 5.19 (m, 1H), 4.51 (bs, 1H), 3.86 (m, 1H), 3.30 (s, 3H), 3.10 (bs, 1H), 3.00 (s, 3H), 2.99-2.87 (m, 4H), 1.68 (m, 1H), 1.50 (d, J=7.15 Hz, 3H), 1.40 (d, J=6.77 Hz, 3H). LCMS (M+H)=654.28.

EXAMPLE 2

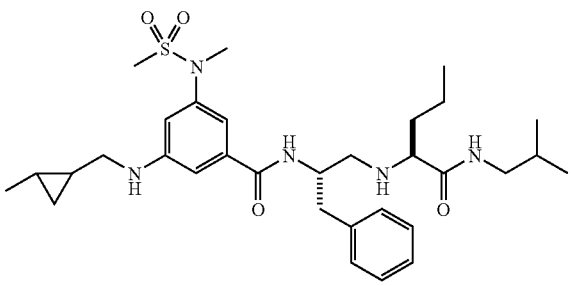

Step A: To 3-amino-5-nitrobenzoic acid (3.60 g, 19.78 mmol) in 100 mL MeOH was added thionyl chloride (2,59 g, 21.76 mmol). The solution was heated to 65° C. for 12 h. Concentration in vacuo afforded the 4.57 g of the methyl ester hydrochloride salt. ¹H NMR (CD₃OD) δ 8.62 (s, 1H), 8.28 (s, 1H), 8.19 (s, 1H), 3.99 (s, 3H).

Step B: To a solution of 3.53 g (18.0 mmol) amino ester from step A in 100 mL CH₂Cl₂/pyridine (3:1) was added methanesulfonyl chloride (2.07 g, 18.0 mmol). The reaction was stirred at ambient temperature for 1 h followed by evaporation of the solvent. The gummy residue was taken up in EtOAc (100 mL), acidified with 1N HCl (100 mL), and extracted with EtOAc (3×100 mL). The combined organic extracts were dried over MgSO₄, filtered, and concentrated in vacuo to provide 3.97 of the sulfonamide as an off-white solid. ¹H NMR (CD₃OD) δ 8.46 (s, 1H), 8.30 (s, 1H), 8.18 (s, 1H), 3.97 (s, 3H), 3.09 (s, 3H).

Step C: Sodium Hydride (0.26 g, 6.55 mmol, 60% oil dispersion) was suspended in 10 mL DMF to which 1.5 g (5.45 mmol) of the sulfonamide from step B in 10 mL DMF was added followed by 0.93 g (6.55 mL) methyl iodide. The solution was stirred at ambient temperature for 3 h. The reaction was quenched with H₂O (250 mL), extracted with EtOAc (3×200 mL), dried over MgSO₄, filtered and concentrated in vacuo. Purification by silica gel chromatography provided 1.43 g of the N-methyl sulfonamide. LCMS (M-H₂O)=272.2

Step D. To a solution of the nitro sulfonamide (2.7 g, mmol) from step C and 0.15 g of 10% Pd/C in 50 mL EtOH containing HOAc (2 mL) was stirred at room temperature under a balloon of hydrogen gas for 12 h. The mixture was filtered through a pad of Celite, concentrated, and purified on silica gel (100% EtOAc) to afford 2.05 g of the desired aniline. ¹H NMR (CD₃OD) δ 7.29 (s, 1H), 7.26 (s, 1H), 6.95 (s, 1H), 3.87 (s, 3H), 3.27 (sm 3H), 2.89 (s, 3H). LCMS (M+H)=258.2

Step E. A solution containing 0.32 g (1.3 mmol) of the aniline from step D, 0.33 g (2.5 mmol) of 1-bromo-2-butyne, and 0.35 g (2.5 mmol) K₂CO₃ in 12.5 mL of acetonitrile was heated at reflux for 4 h The reaction mixture was cooled and diluted with 60 mL of H₂O. The mixture was extracted with of EtOAc (3×60 mL). The combined organics were washed with brine (60 mL) then dried (MgSO₄). The solvent was removed in vacuo and purified by silica gel chromatography (20%-50% EtOAc:Hex) to afford 160.0 mg of alkynyl aniline. LCMS (M+H)=311.2

Step F. A solution containing 83 mg (0.27 mmol) of alkynyl aniline from step E in 3 mL MeOH was treated with a catalytic amount of Lindlar's catalyst and stirred at room temperature under a hydrogen atmosphere for 10 min. The reaction was filtered through plug of silica gel and the solvent was removed in vacuo. Purification by reverse phase HPLC afforded 38 mg of Z-alkenyl aniline. LCMS (M+H)=313.2

Step G. A solution containing 38 mg (0.12 mmol) Z-alkenyl aniline from step F in 2.5 mL EtOAc at 0° C. was treated with 58 mg (1.3 mmol) of freshly prepared diazomethane and a catalytic amount of palladium acetate and stirred at 0° C. for 15 min. The reaction was filtered through a plug of silica gel. Evaporation of the solvent left 34.0 mg of the methyl cyclopropyl methyl aniline. LCMS (M+H)=327.2

Step H. To 34 mg (0.10 mmol) of the methyl cyclopropyl methyl aniline from step G in 5 mL THF:MeOH (1:1) was added 2 N NaOH (0.15 mL, 0.30 mmol). The solution was heated to 50° C. for 1 h. After cooling the solution was acidified by the addition of 1 N HCl (20 mL) and extracted with EtOAc (3×30 mL). The combined organic extracts were dried over MgSO₄, filtered, and concentrated in vacuo to yield 0.020 g of the desired carboxylic acid. LCMS (M+H)=313.2

Step I. A solution containing 31.3 mg (0.10 mmol) of the carboxylic acid from step H, 37.6 mg (0.1 mmol) of intermediate diamine II, 44.4 mg (0.1 mmol) of BOP reagent and 0.076 mL (0.44 mmol) of Hunig's base were stirred at rt for 1 h in 5 mL of DCM. The solvent was evaporated and the residue was purified by reverse phase chromatography to afford 35 mg of the title compound as a white solid. ¹H NMR (CD₃OD) δ 7.32-6.98 (m, 8H), 4.59 (m, 1H), 4.14-4.07 (m, 1H), 3.84 (m 1H), 3.36 (s, 3H), 3.33 (m, 2H), 3.31 (s, 3H), 3.24-3.07 (m, 2H), 3.01 (m, 2H), 2.92 (m, 3H), 2.03 (m, 2H), 1.87-1.63 (m, 4H), 1.25 (m, 1H), 1.07 (m, 2H), 0.97 (m, 3H), 0.92 (d, J=6.6 Hz, 6H), 0.83-0.76 (m, 1H). LCMS (M+H)=600.32

EXAMPLE 3

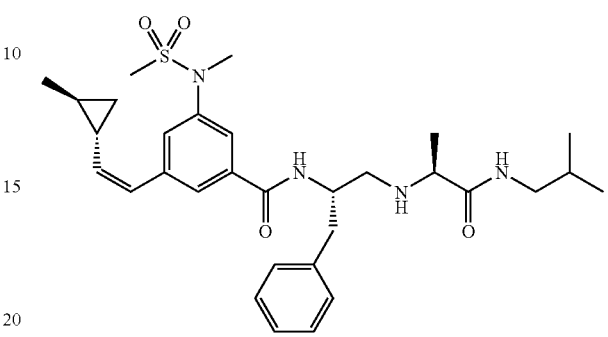

Step A: 3-Nitrobenzoate (35.3 g, 195 mmol) in triflic acid (100 mL) at 0° C. was added NIS (43.8 g, 195 mmol) in ten portions. Remove ice bath and stir for 48 hrs. The reaction typically goes to 50% completion. At this time more NIS could be added or cool to 0° C. and quench with careful dropwise addition of water. The mixture was extracted three times with EtOAc (250 mL) and the combined extracts were washed with a 10% NaHSO₃ solution, followed by water. The organics were dried over Na₂SO₄, concentrated, and purified on silica gel (10% EtOAc in Hex) affording 24.1 g.

Step B: Tin chloride (88.6 g, 392 mmol) in EtOH (50 mL) was refluxed and the nitrobenzoate from step A (24.1 g, 78.4 mmol) in 1:1 THF:EtOH (100 mL) was added dropwise. The reaction mixture was refluxed for 30 minutes then cooled to 0° C. The resulting solution was basified to pH 8-9 with aq. Na₂CO₃. The aqueous layer was extracted three times with EtOAc (700 mL) and the combined extracts were washed with saturated NaHCO₃ then brine. The organics were dried over Na₂SO₄ and concentrated to afford 21.7 g of the crude aniline which was used without further purification.

Step C: To a 0° C. solution of aniline from step B (21.7 g, 78.3 mmol) in 3:1 CH₂Cl₂:pyridine (75 mL) was added methanesulfonyl chloride (6.36 mL, 82.2 mmol). The ice bath was removed after 15 minutes and the solution was stirred overnight at room temperature. The reaction mixture was extracted several times with 1N HCl. The organic phase was dried, concentrated, and chromatographed (1:1 EtOAc: Hex) to afford 25.2 g of the desired sulfonamide as a white solid.

Step D: The sulfonamide from step C (23.6 g, 66.5 mmol) in DMF (75 mL) at 0° C. was treated with 60% NaH (2.92 g, 73.1 mmol). The solution stirred for 30 minutes before MeI (4.55 mL, 73.1 mmol) was added. The ice bath was removed and the solution was stirred at rt for twelve hours. The reaction was quenched with saturated NH₄Cl solution and extracted three times with EtOAc (150 mL). The combined organic were washed with water (5×50 mL), dried, concentrated to afford 25.3 g of the desired methylated anilide which was used without further purification.

Step E: Trans-2-methylcyclopropanemethanol (7.0 g, 81 mmol) was added to a solution of PCC (28 g, 130 mmol) in CH₂Cl₂ (225 mL). The solution became black and was stirred for three hours at room temperature. The reaction mixture was diluted with ether (250 mL) and decanted. The liquid solution was filtered through a 4 inch plug of Florisil and the solvent was removed by distillation through a Vigreux column to afford 10 g of the desired aldehyde.

Step F: To a solution of PPh$_3$ (12.4 g, 47.5 mmol) in CH$_2$Cl$_2$ (100 mL) at 0° C. was added CBr$_4$ (7.88 g, 23.7 mmol). The reaction mixture was stirred for 10 minutes then treated with the carboxaldehyde from step E (1.0 g, 12 mmol). The solution was stirred for 30 minutes at 0° C. then 1 hr at room temperature. Hexane was added and the solids were filtered, and the filtrate was concentrated to afford 4.4 g of the dibromide.

Step G: The dibromide from step F (15.4 g, 64.1 mmol) in 60 mL of cyclohexane at −78° C. was treated with 2.0 M n-BuLi in cyclohexane (64.1 mL, 128 mmol). The resulting reaction mixture was stirred at −78° C. for 1 hr then warmed to room temperature where it was stirred for 2 hr. The reaction was quenched with water and extract with cyclohexane (3×25 mL). The product was purified by distillation (bp=69-72 C).

Step H: A 100 mL 3-neck round bottom flask was charged with InCl$_3$ (0.829 g, 10.4 mmol) and dried under vacuum with a heat gun for 2 minutes. THF (16 mL) was added under nitrogen and the flask was immersed in a −78° C. ice bath. DIBAL-H (12.4 mL, 1M in hexanes) was then added dropwise and the resulting solution was stirred for 30 minutes at −78° C. After this time, the acetylene from step G (10.4 mmol) was added followed by 1.0 M Et$_3$B (1.6 mL, 1M in hexanes). This reaction mixture was stirred at −78° C. for 2.5 hr then warmed to room temperature. DMI (12 mL) and aryliodide from step D (1.47 g, 4.0 mmol) was added followed by a palladium trifurylphosphine complex [prepared from Pd$_2$(DBA)$_3$° CHCl$_3$ (20 mg) and trifurylphosphine (28 mg) in THF (6 mL)]. The resulting reaction mixture was heated at 60° C. for 2 hr, quenched with water and extracted with ether (3×50 mL). The combined organic extracts were dried, and concentrated and the product was purified on a chiral OJ column (60:40 Hexane w/0.1% TFA:EtOH). Collection of the first peak afforded 276 mg of the desired diastereomer.

Step I: To 276 mg (0.853 mmol) of the ester from step H in 10 mL THF:MeOH:water (3:1:1) was added 2 N NaOH (0.64 mL, 1.28 mmol). The solution was stirred at rt for 2 h. The reaction mixture was concentrated and acidified with 2 N HCl (10 mL) and extracted with CHCl$_3$ (3×20 mL). The combined organic extracts were dried over MgSO$_4$, filtered, and concentrated to yield 253 mg of the desired carboxylic acid. LCMS (M+H)=310.12

Step J: A solution containing 8.0 mg (0.026 mmol) of the carboxylic acid from step I, 10.6 mg (0.031 mmol) of intermediate diamine IV, 11.4 mg (0.026 mmol) of BOP reagent and 0.026 mL (0.11 mmol) of Hunig's base was stirred at rt for 1 h in 3 mL of DCM. The solvent was evaporated and the residue was purified by reverse phase chromatography to afford 17.6 mg of the title compound as a white solid. 1H NMR (400 MHz, CDCl$_3$) δ 7.95 (bd, H), 7.62-7.57 (m, 3H), 7.33-7.22 (m, 4H), 6.74 (s, 1H), 6.21 (d, 1H), 5.15 (dt, 1H), 4.66 (m, 1H), 3.96 (bd, 1H), 3.48-3.39 (m, 4H), 3.09-2.95 (m, 5H), 2.86 (s, 1H), 1.56-1.44 (m, 5H), 1. (m, 2H), 1.12-1.11 (d, 3H), 0.92-0.84 (m, 7H), 0.66-0.62 (m, 2H). LCMS (M+H)=569.2

The following compounds were prepared in a manner similar to the title compounds of the foregoing examples using appropriate starting materials and reagents.

| Ex | Structure |
|---|---|
| 4 | 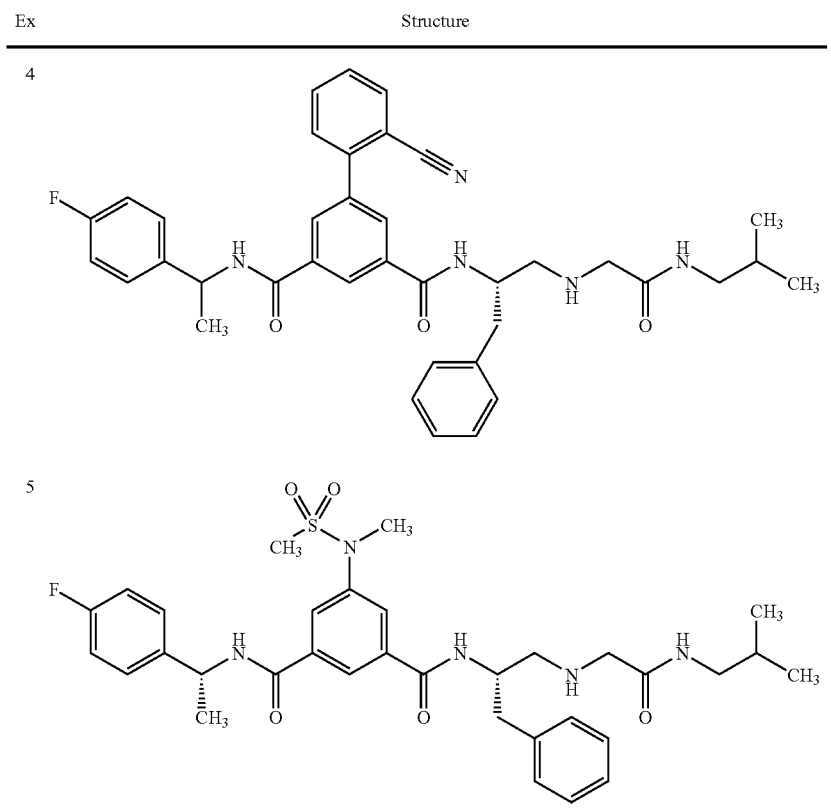 |
| 5 | 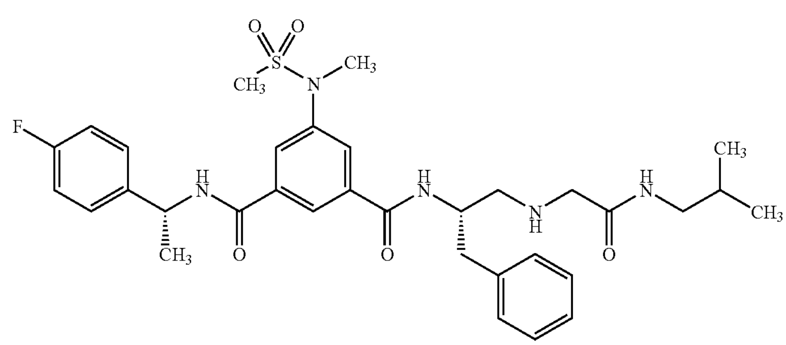 |

-continued

| Ex | Structure |
|---|---|
| 6 | 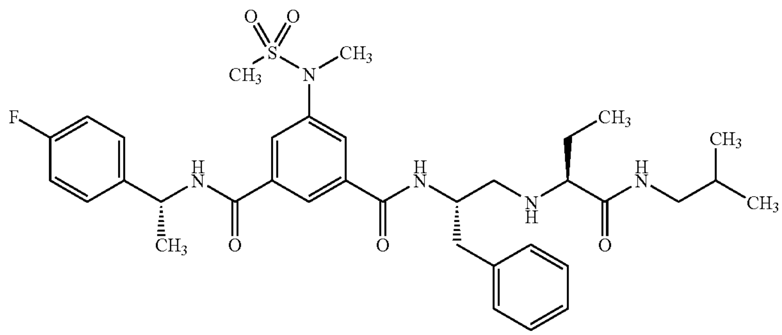 |
| 7 | 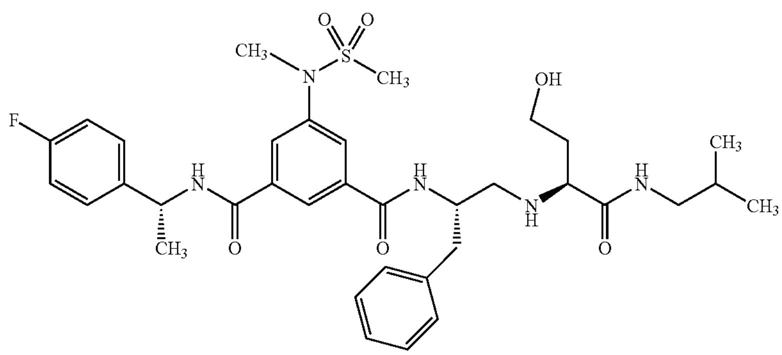 |
| 8 | 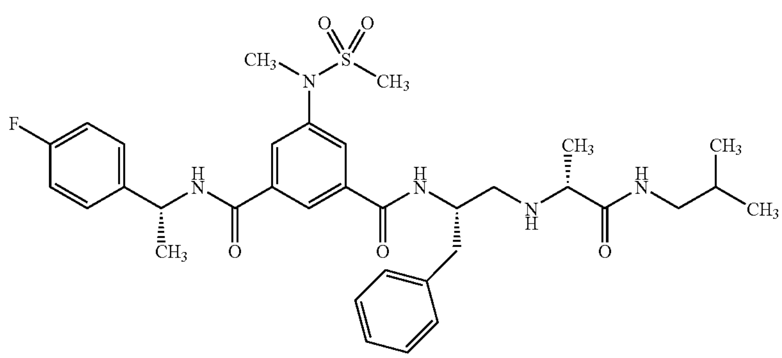 |
| 9 | 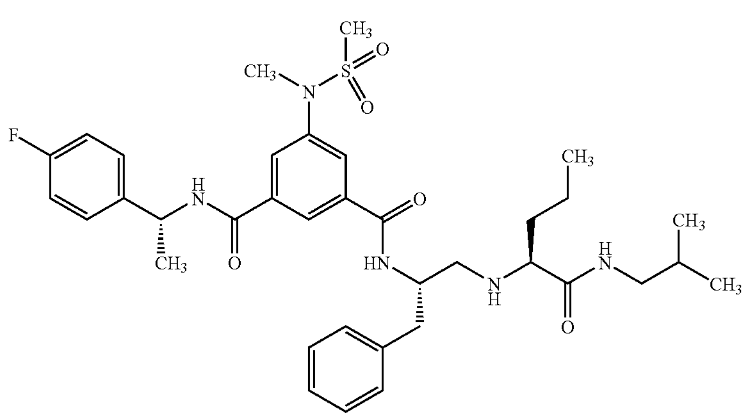 |

-continued
| Ex | Structure |
|---|---|
| 10 | 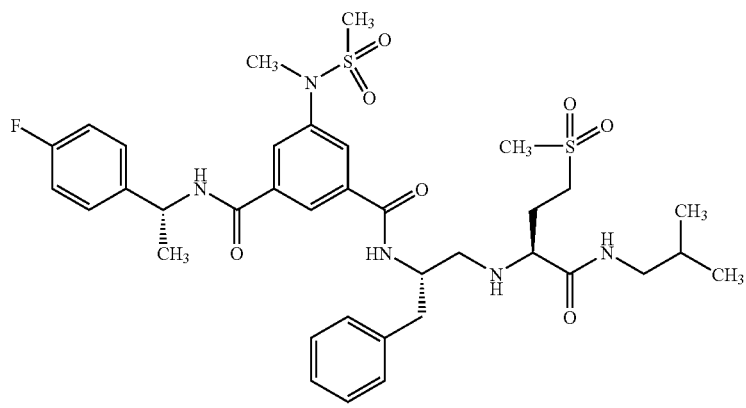 |
| 11 | 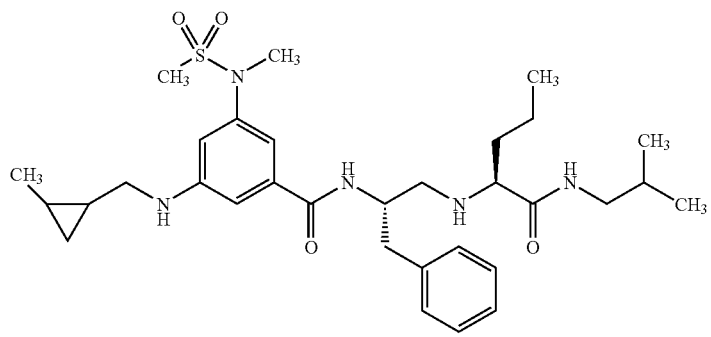 |
| 12 | 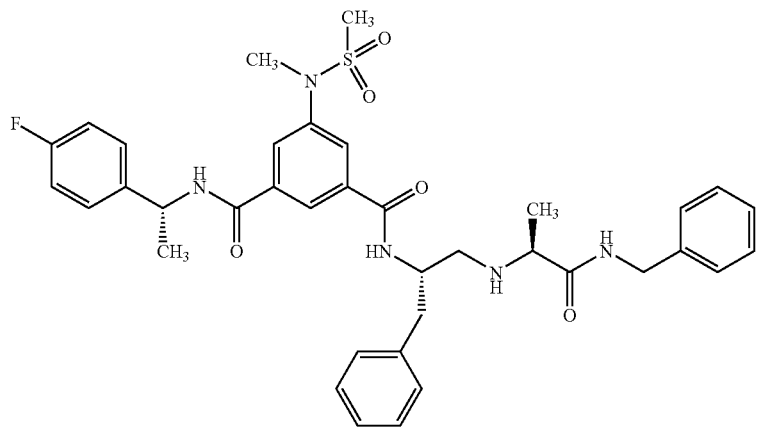 |

| Ex | Structure |
|---|---|
| 13 | 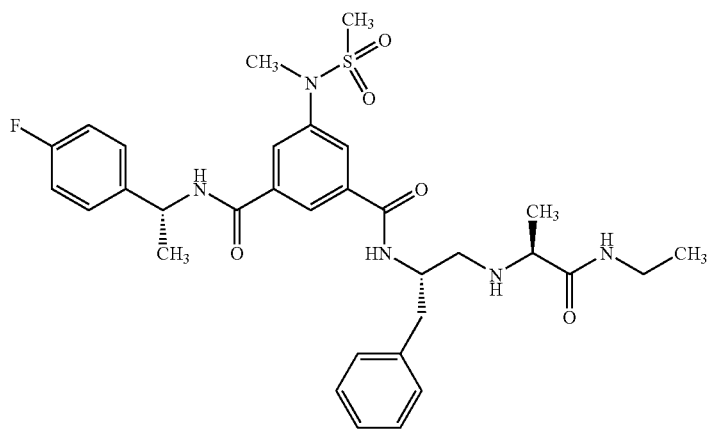 |
| 14 | 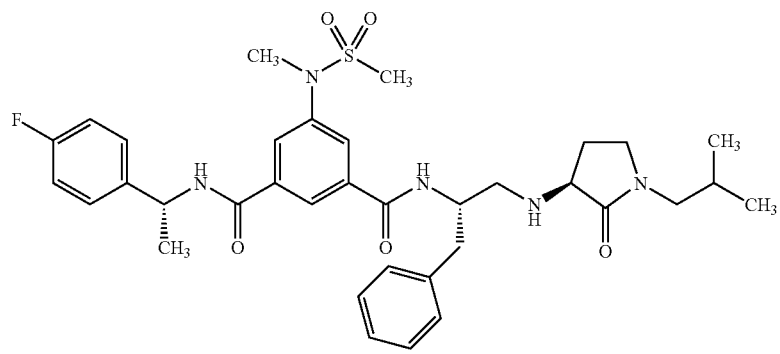 |
| 15 | 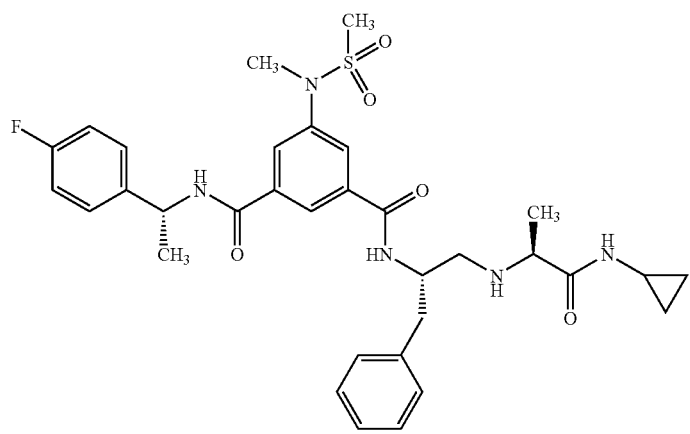 |

-continued
| Ex | Structure |
|---|---|
| 16 | 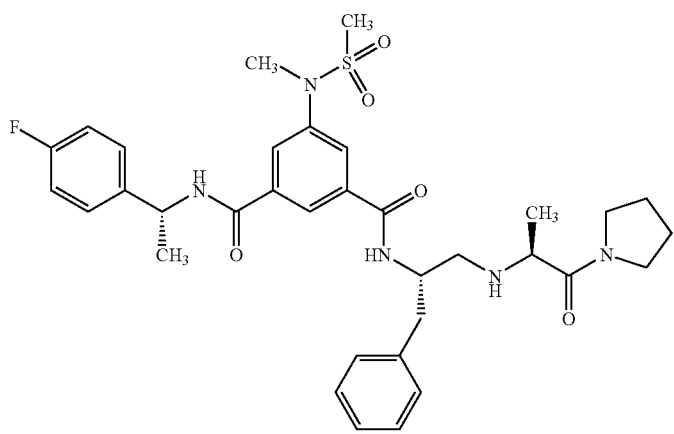 |
| 17 | 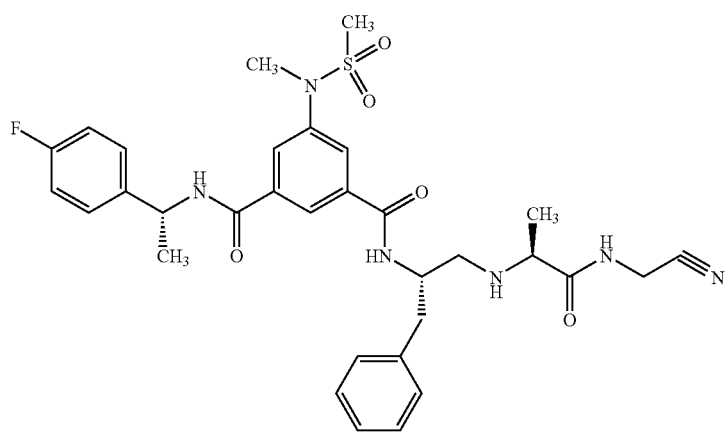 |
| 18 | 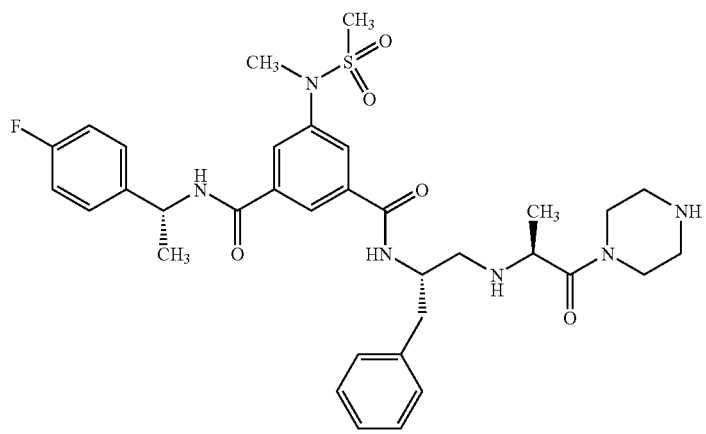 |

-continued

| Ex | Structure |
|---|---|
| 19 | 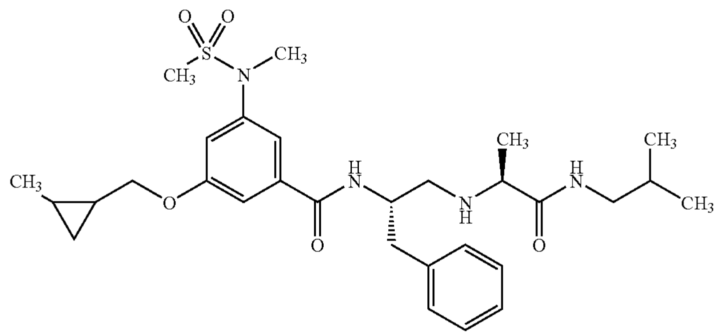 |
| 20 | 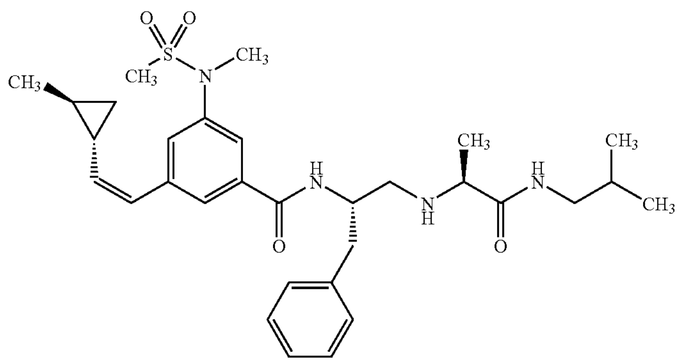 |
| 21 | 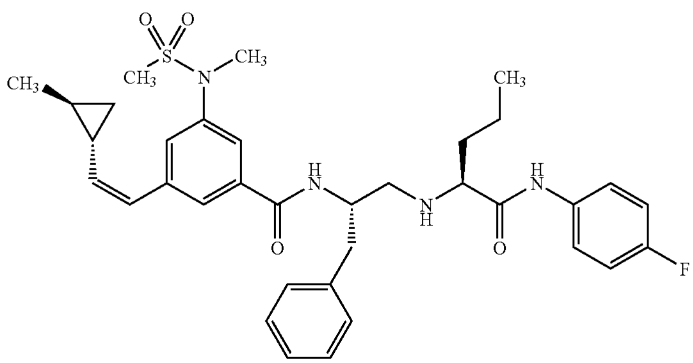 |
| 22 | 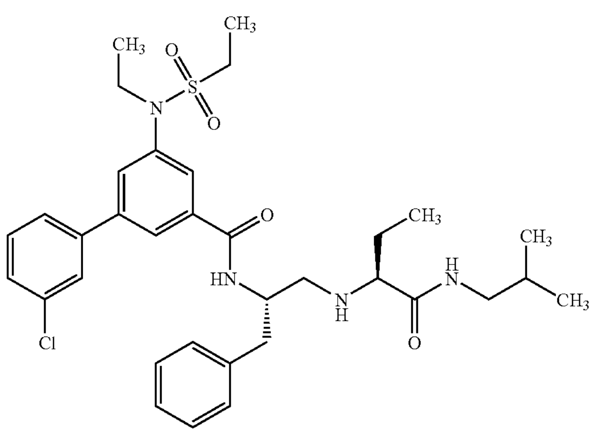 |

| Ex | Structure |
|---|---|
| 23 | 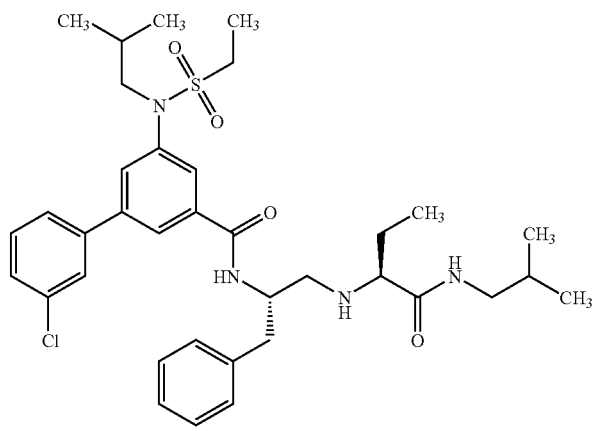 |
| 24 | 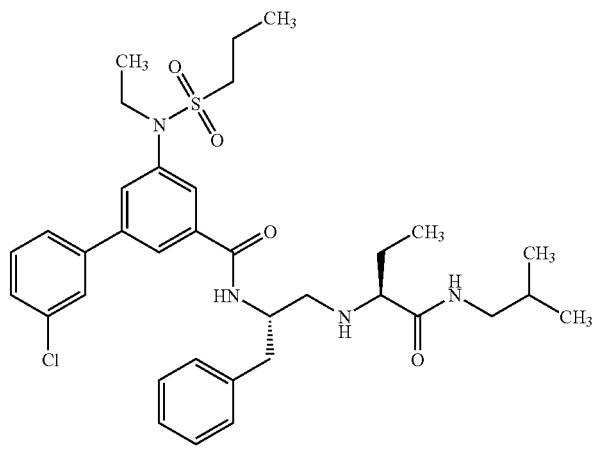 |
| 25 | 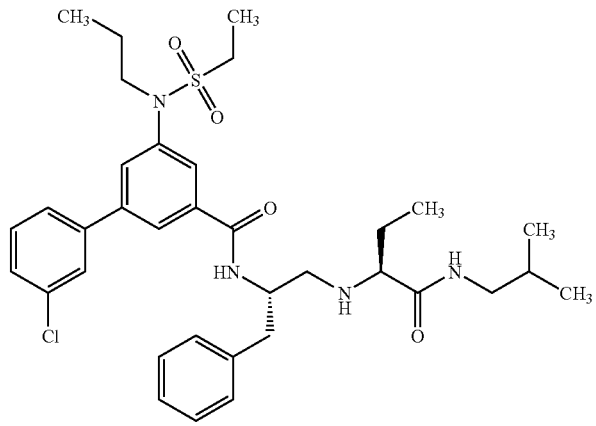 |

| Ex | Structure |
|---|---|
| 26 | 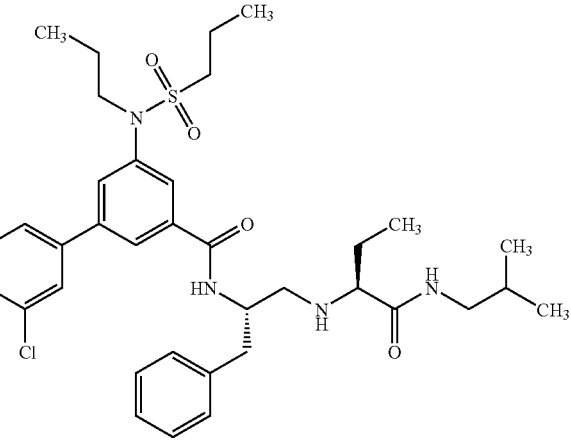 |
| 27 | 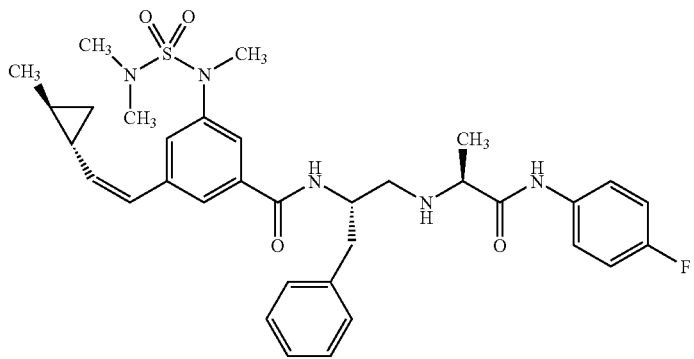 |
| 28 | 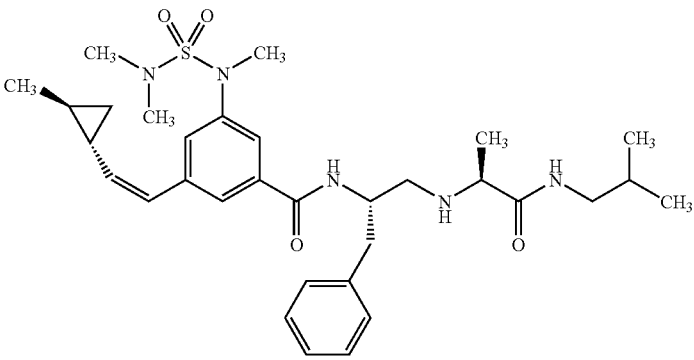 |
| 29 | 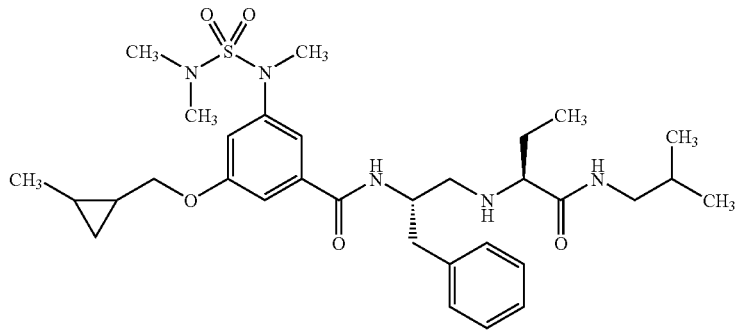 |

-continued
| Ex | Structure |
|---|---|
| 30 | 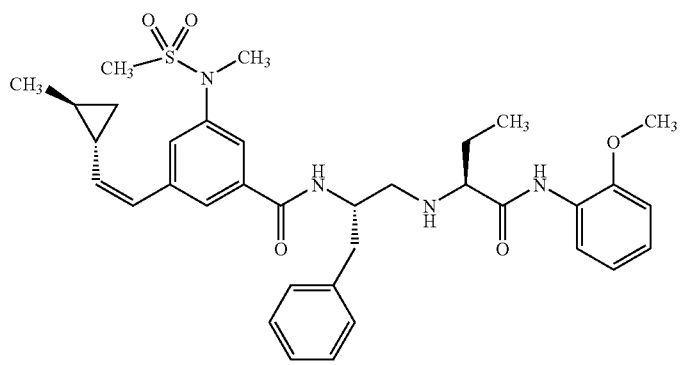 |
| 31 | 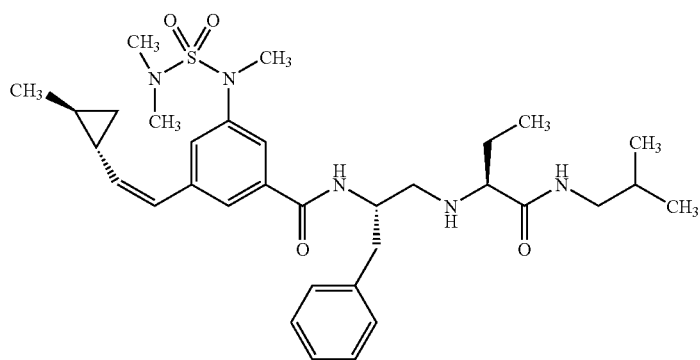 |
| 32 | 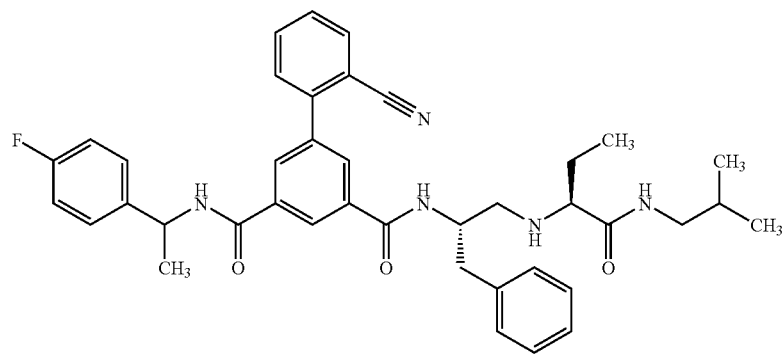 |
| 33 | 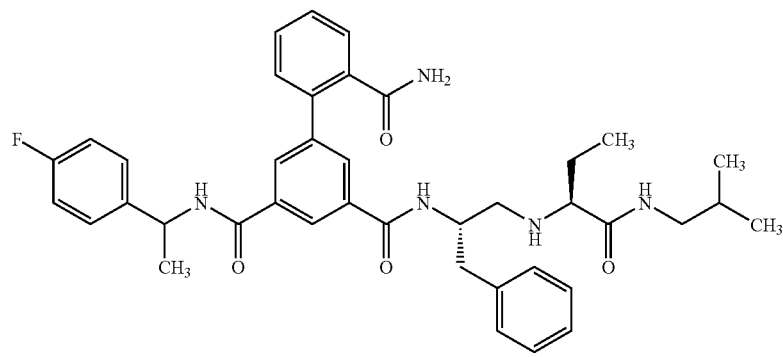 |

| Ex | Structure |
|---|---|
| 34 | 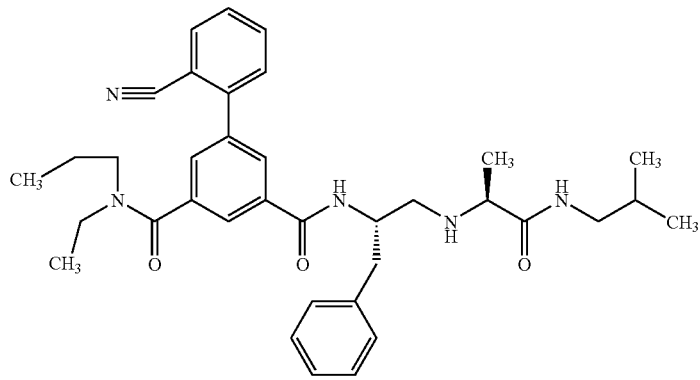 |
| 35 | 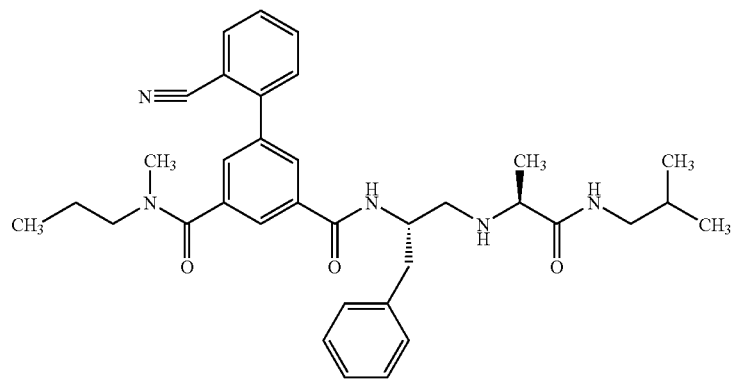 |
| 36 | 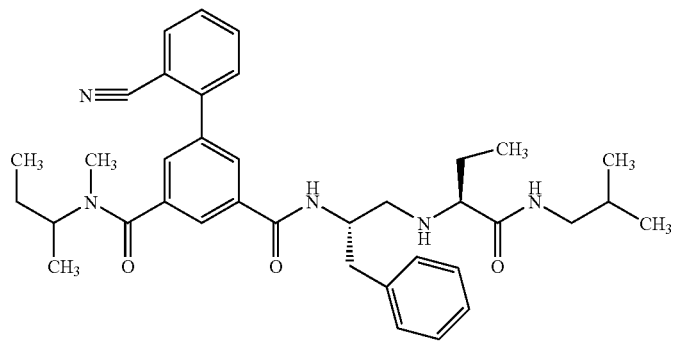 |
| 37 | 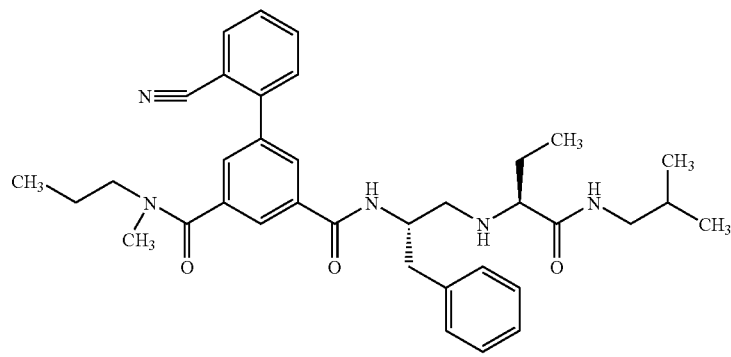 |

-continued

| Ex | Structure |
|---|---|
| 38 | 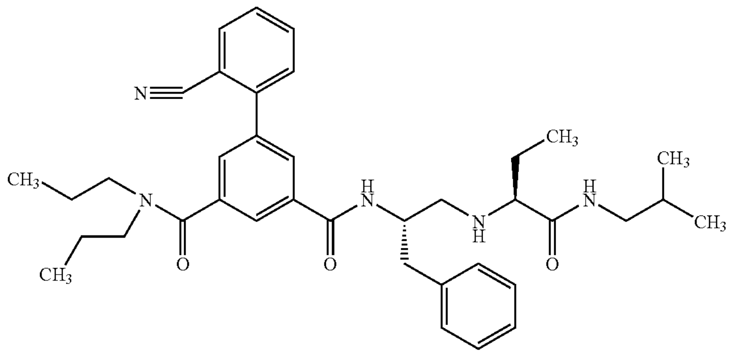 |
| 39 | 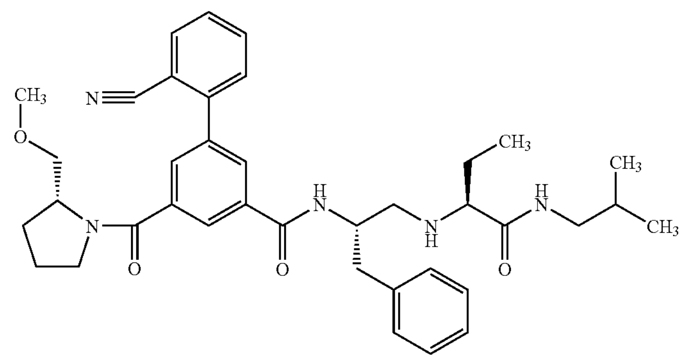 |
| 40 | 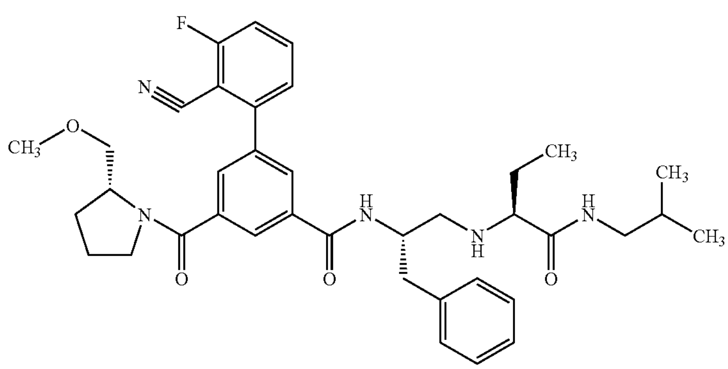 |
| 41 | 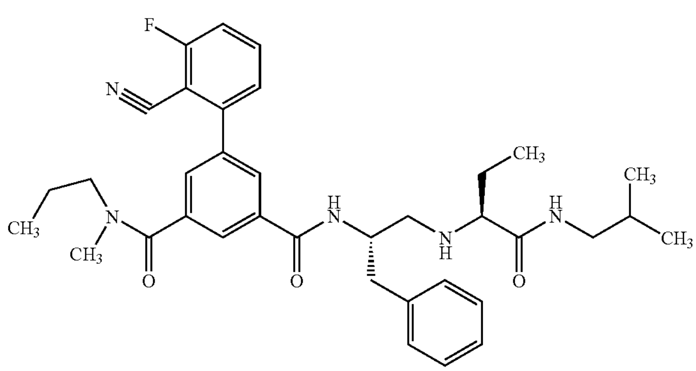 |

| Ex | Structure |
|---|---|
| 42 | 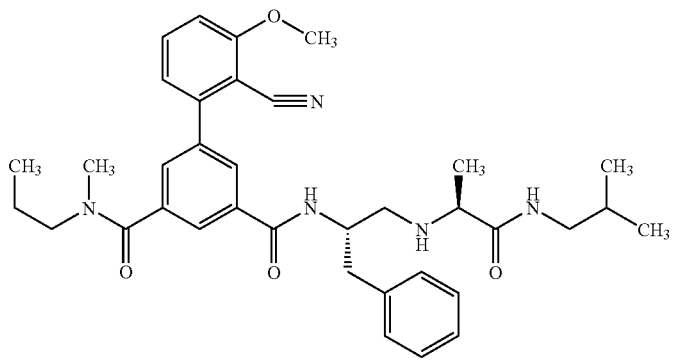 |
| 43 | 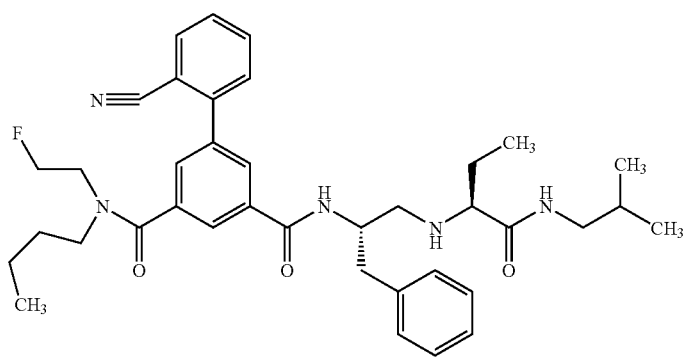 |
| 44 | 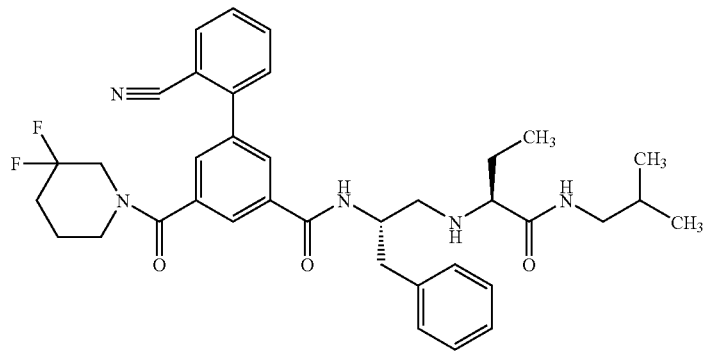 |
| 45 | 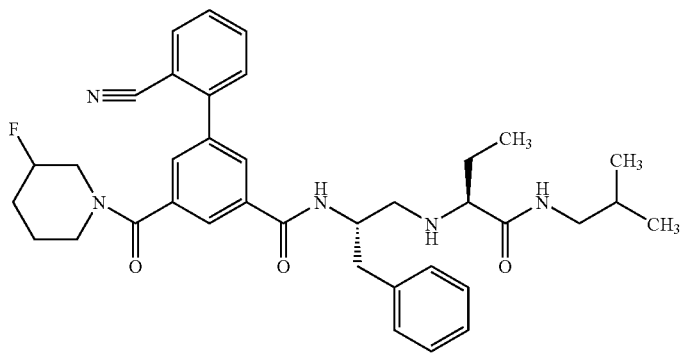 |

-continued
| Ex | Structure |
|---|---|
| 46 | 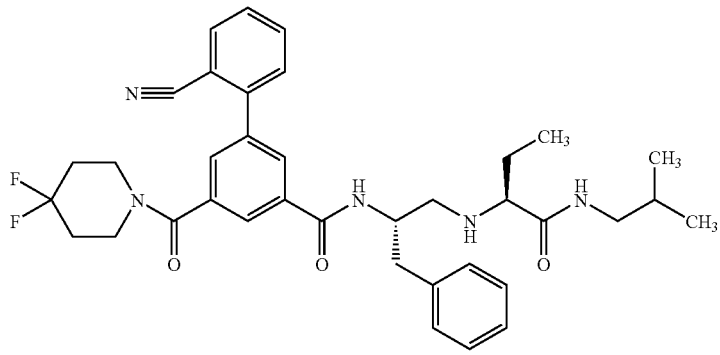 |
| 47 | 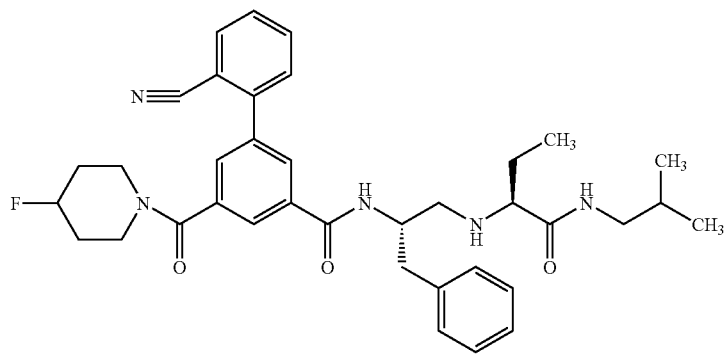 |
| 48 | 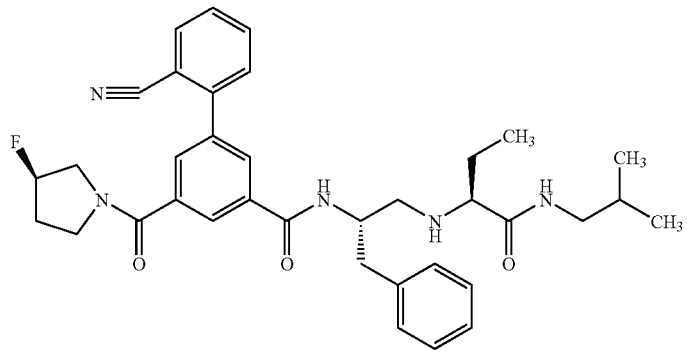 |
| 49 | 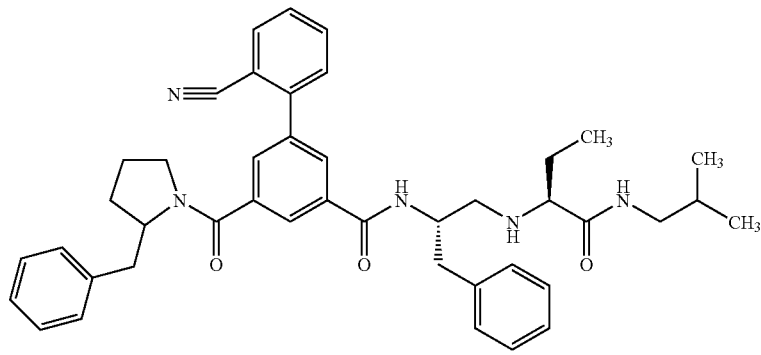 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of the formula I:

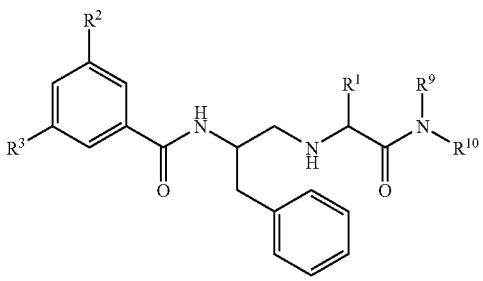

wherein:

$R^1$ is selected from the group consisting of:
(1) $C_{1-6}$alkyl, unsubstituted or substituted with —$OR^5$ or —$S(O)_2$—$C_{1-6}$alkyl,
(2) hydrogen,
(3) phenyl, and
(4) benzyl;

$R^2$ is selected from the group consisting of:
(1) $R^4$—$S(O)_p$—,
   wherein $R^4$ is independently selected from the group consisting of:
      (a) —$C_{1-6}$alkyl, which is unsubstituted or substituted with 1-6 fluoro,
      (b) phenyl, and
      (c) benzyl,
(2) $R^4$—$S(O)_pN(R^5)$—,
   wherein $R^5$ is independently selected from the group consisting of:
      (a) hydrogen,
      (b) —$C_{1-6}$alkyl, which is unsubstituted or substituted with 1-6 fluoro,
      (c) —$C_{3-6}$cycloalkyl which is unsubstituted or substituted with methyl,
      (d) phenyl, which is unsubstitued or substituted with halo or methoxy, and
      (e) benzyl,
(3) —CN,
(4) —$C_{1-6}$alkyl-CN,
(5) halogen,
(6)

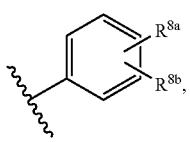

wherein $R^{8a}$ and $R^{8b}$ are independently selected from the group consisting of:

(a) hydrogen,
(b) —CN,
(c) halo,
(d) —$C_{1-6}$alkyl,
(e) —O—$R^5$,
(f) —S—$R^5$,
(g) —$CO_2R^5$, and
(h) tetrazolyl, (7)

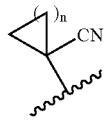

wherein n is 1, 2, 3 or 4;

$R^3$ is selected from the group consisting of:

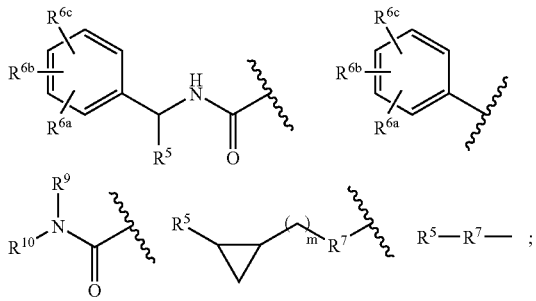

$R^{6a}$, $R^{6b}$, and $R^{6c}$ are independently selected from the group consisting of:
(1) hydrogen,
(2) halogen,
(3) —$OR^5$,
(4) —$SR^5$, and
(5) —$C_{1-6}$alkyl;

$R^7$ is selected from the group consisting of a bond, —CH=CH—, —O—, —S—, and —NH—;

$R^9$ and $R^{10}$ are independently selected from the group consisting of:
(1) hydrogen,
(2) $C_{1-6}$alkyl, unsubstituted or substituted with —CN or 1-4 halo,
(3) —$C_{3-6}$cycloalkyl,
(4) phenyl, which is unsubstitued or substituted with halo or methoxy, and
(5) benzyl,
or $R^9$ and $R^{10}$ may be joined together to form a pyrrolidine or piperidine ring which is unsubstituted or substituted with benzyl, —$OR^5$ or 1-4 halo;

m is independently 0, 1, or 2;

p is independently 0, 1, or 2, and pharmaceutically acceptable salts thereof.

2. The compound of claim 1 wherein $R^1$ is $C_{1-6}$alkyl.

3. The compound of claim 1 wherein $R^1$ is methyl.

4. The compound of claim 1 wherein $R^1$ is ethyl.

5. The compound of claim 1 wherein $R^2$ is:

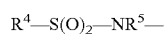

$R^4$—$S(O)_2$—$NR^5$— and wherein $R^4$ is selected from the group consisting of:
(1) $C_{1-6}$alkyl,
(2) phenyl, and
(3) benzyl;

$R^5$ is selected from the group consisting of:
(1) $C_{1-6}$alkyl,
(2) phenyl,
(3) benzyl, and
(4) hydrogen.

6. The compound of claim 1 wherein $R^3$ is:

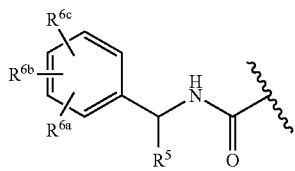

and wherein $R^5$ is methyl, $R^{6a}$ is H or F, $R^{6b}$ and $R^{6c}$ are hydrogen.

7. The compound of claim 1 wherein $R^3$ is:

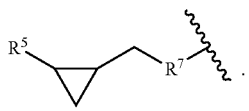

8. The compound of claim 1 wherein $R^9$ is hydrogen.
9. The compound of claim 1 wherein $R^{10}$ is $C_{1-6}$alkyl.
10. The compound of claim 1 wherein $R^{10}$ is iso-butyl.
11. A compound which is selected from the group consisting of:

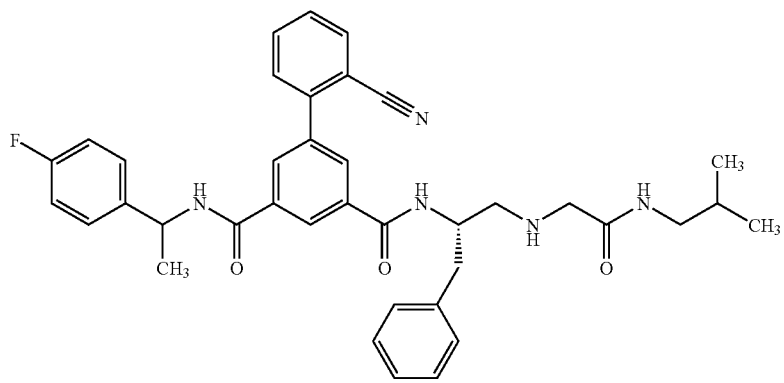

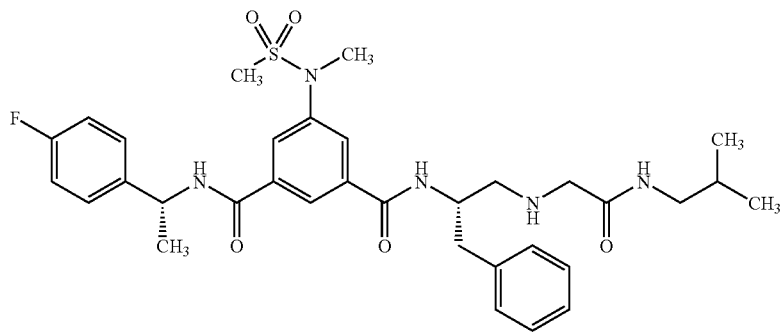

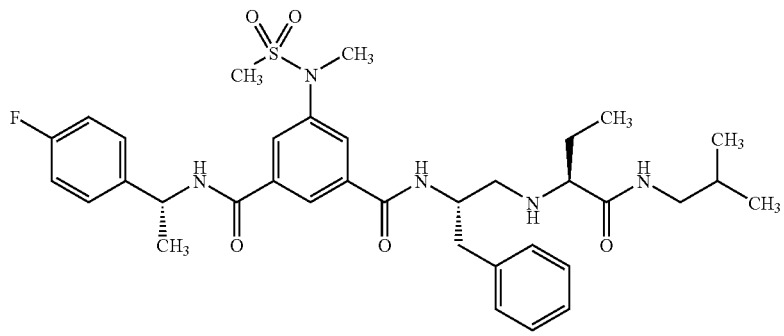

-continued
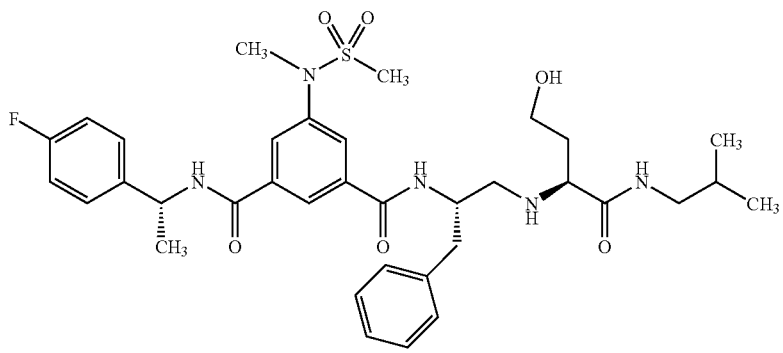
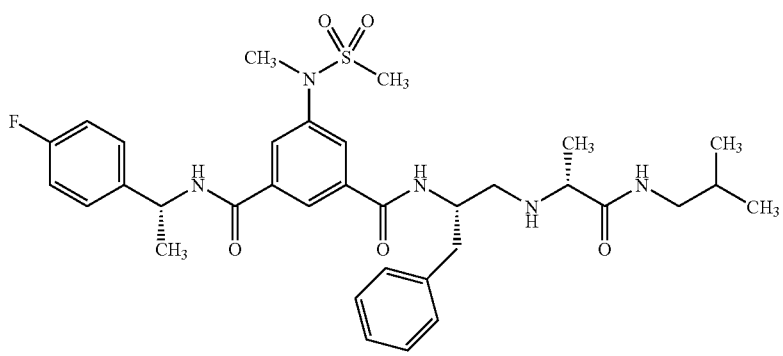
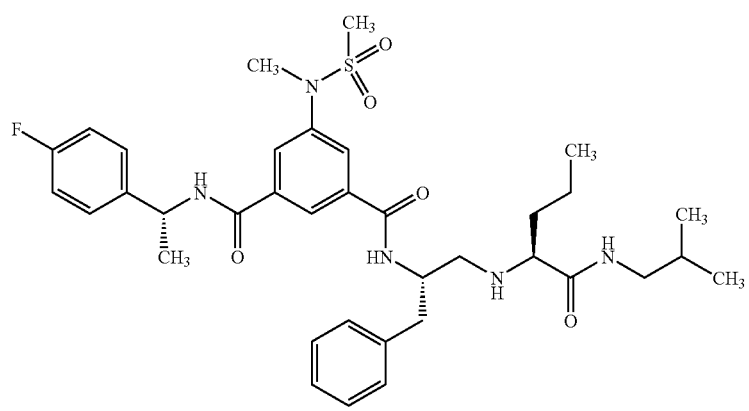
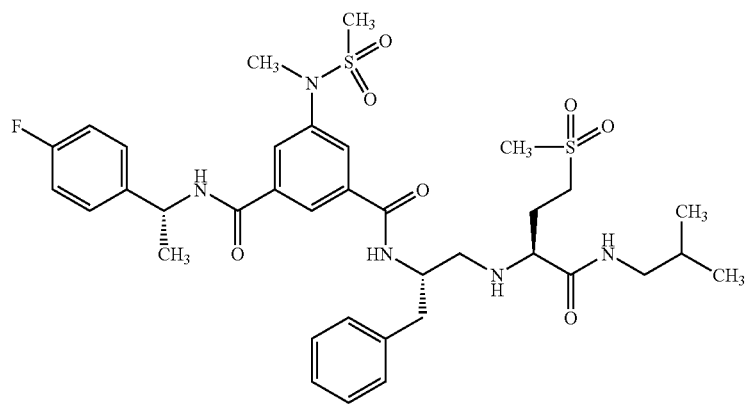

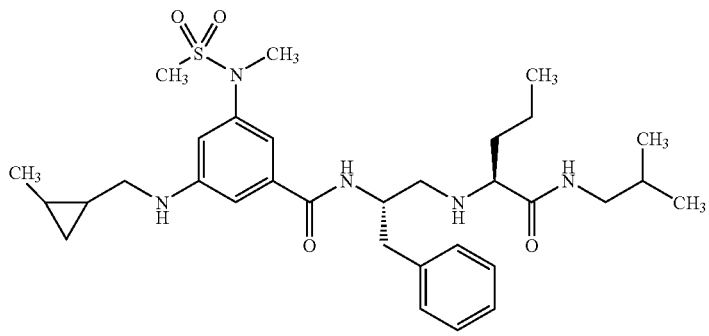
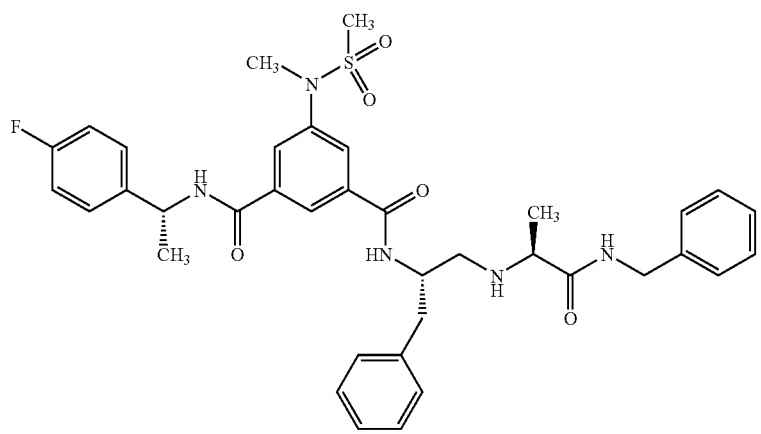
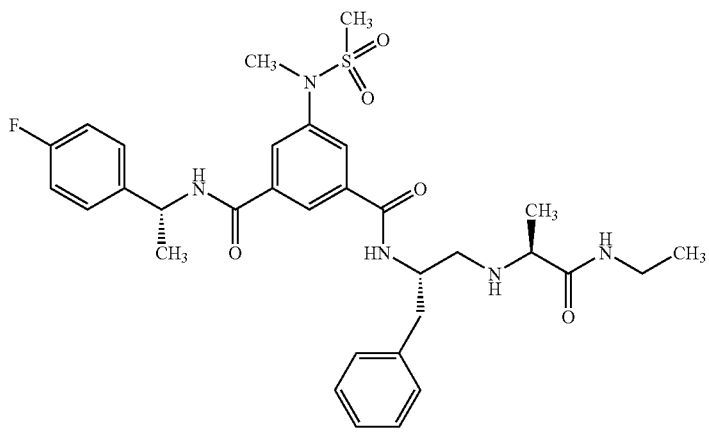
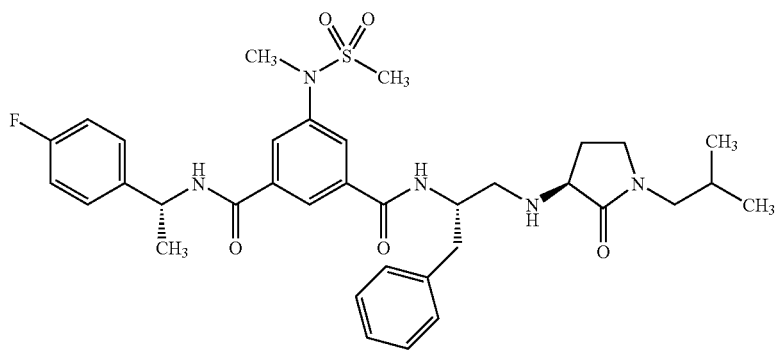

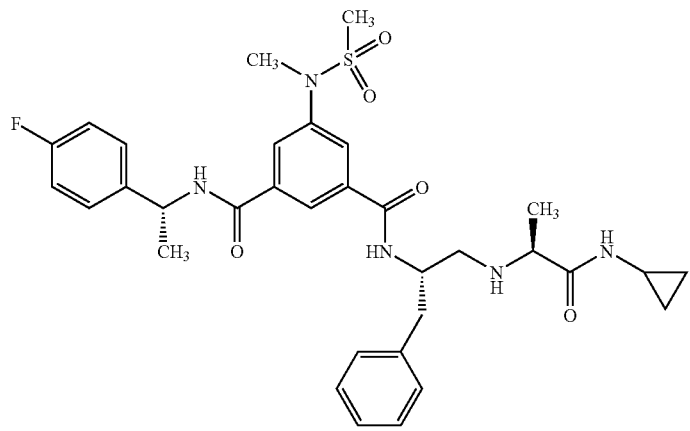
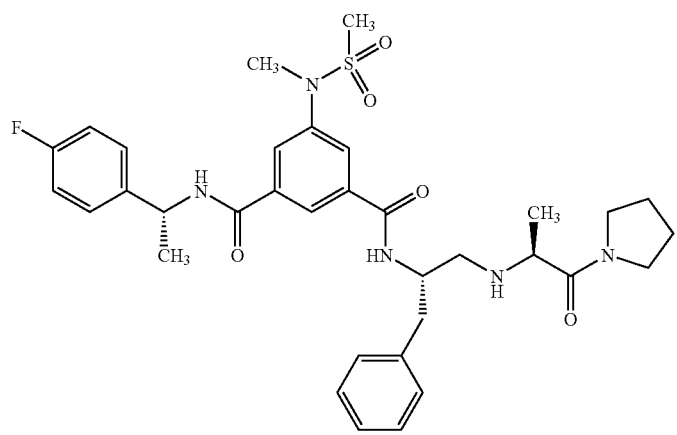
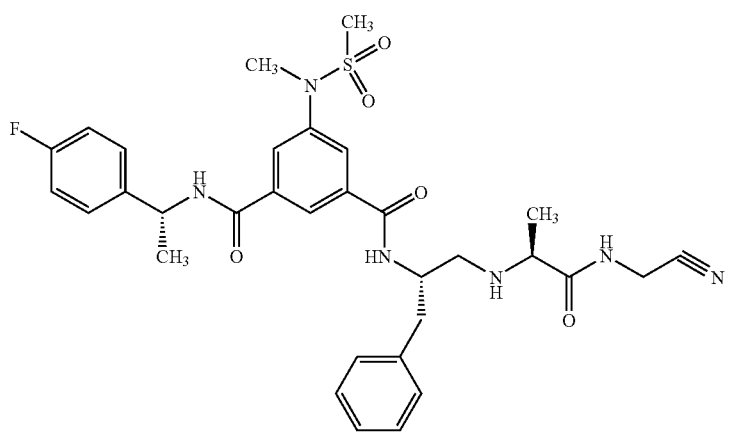

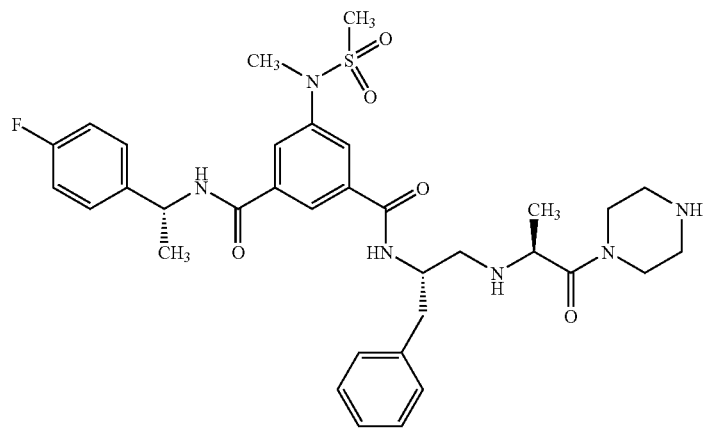
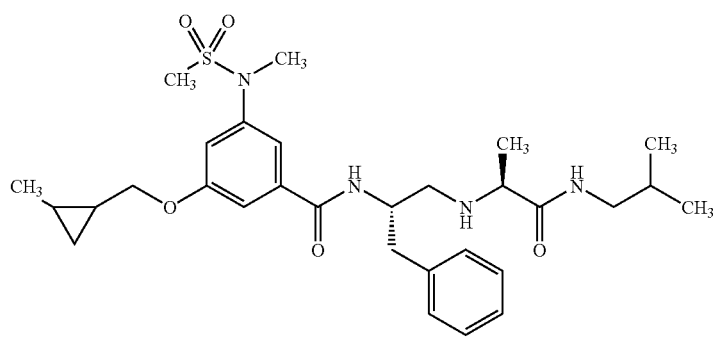
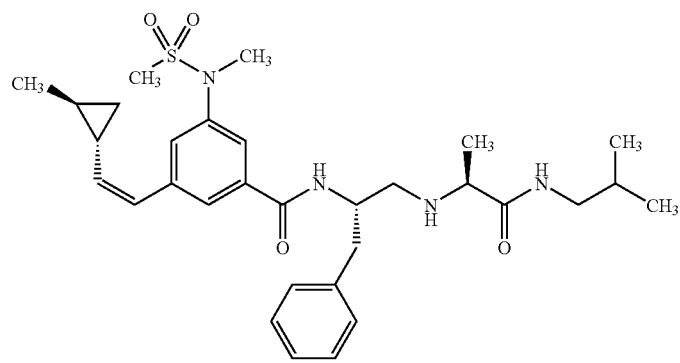
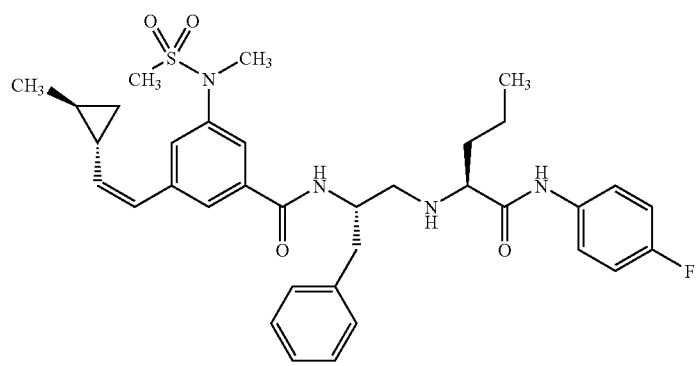

-continued
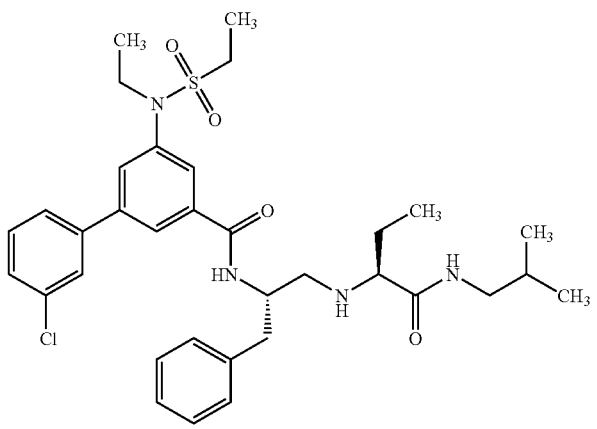
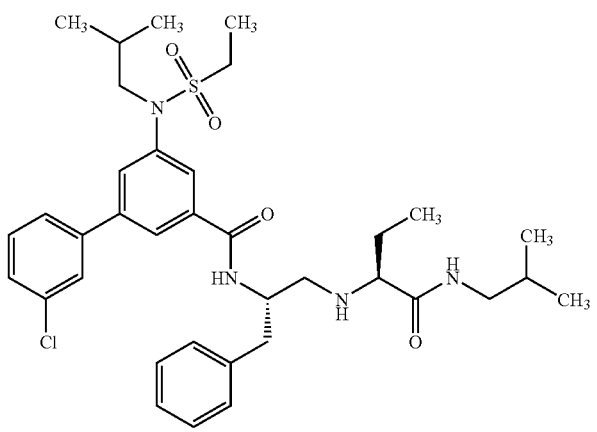
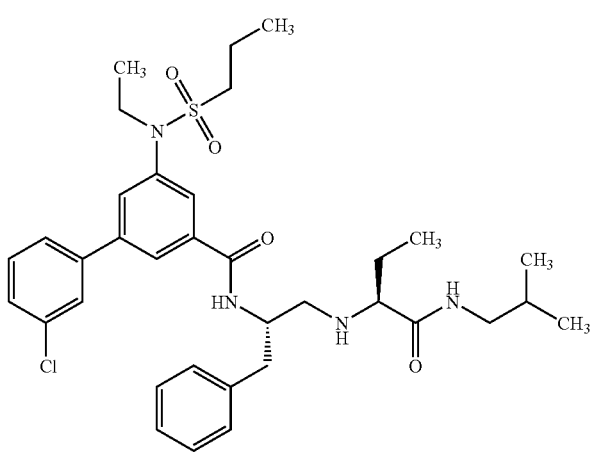

-continued
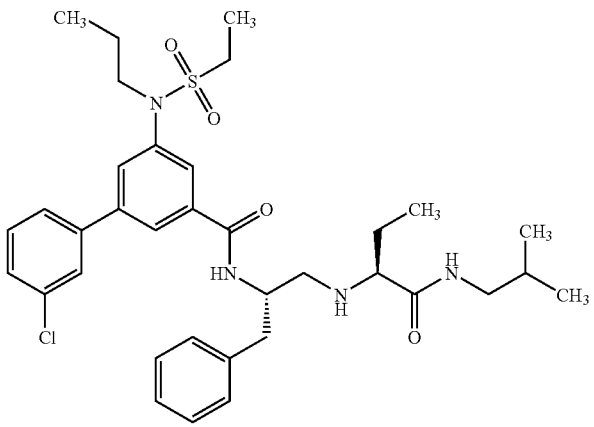
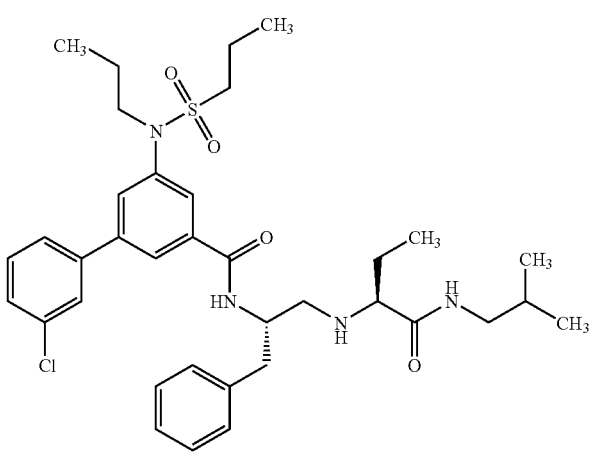
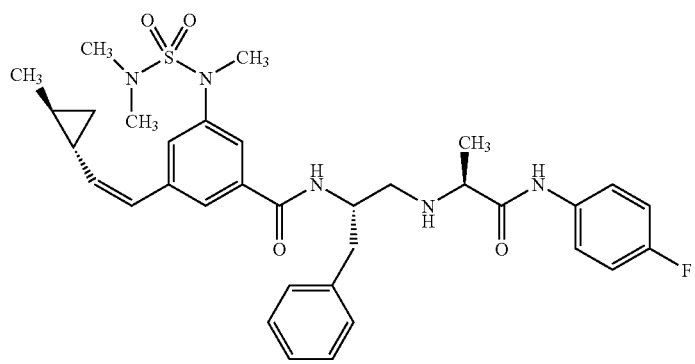
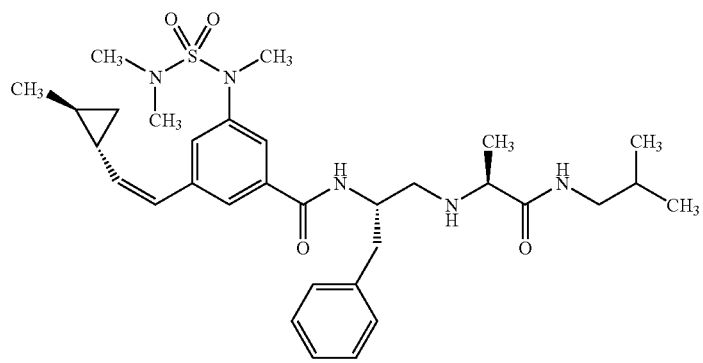

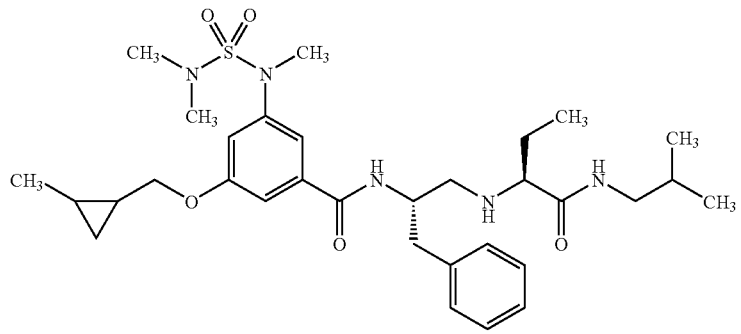
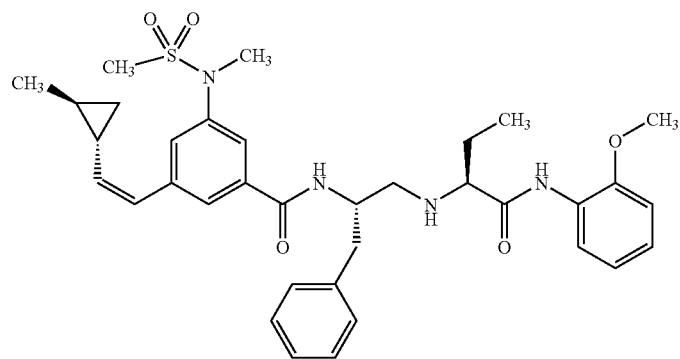
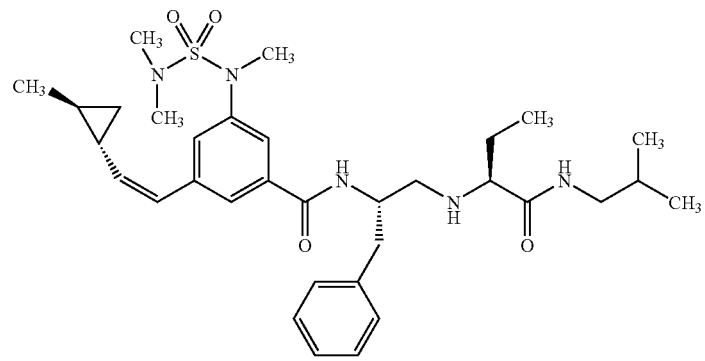
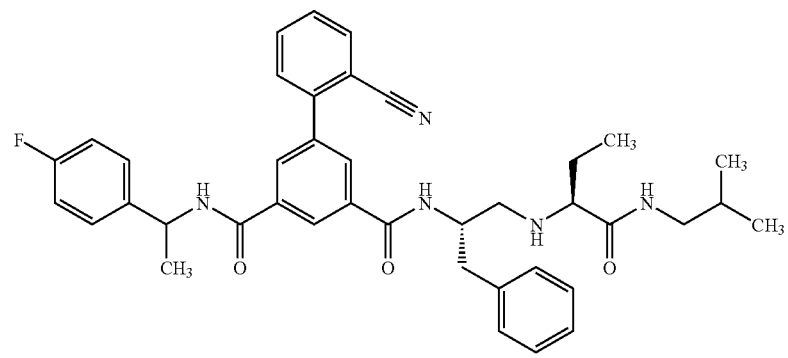

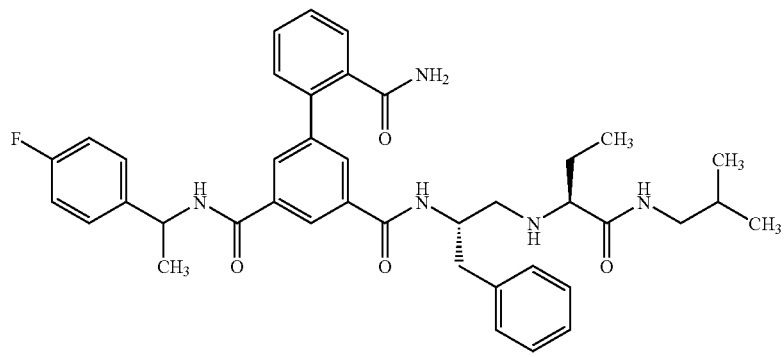
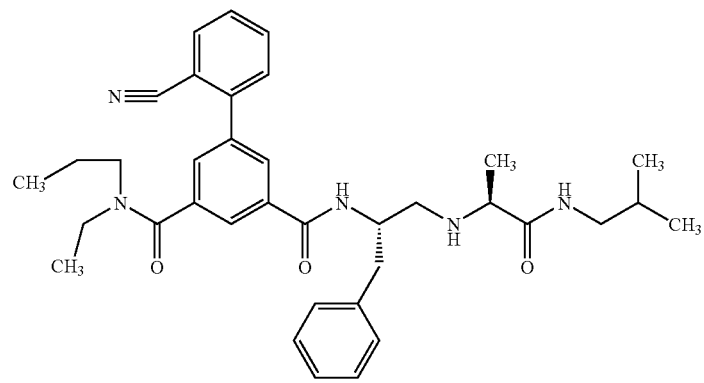
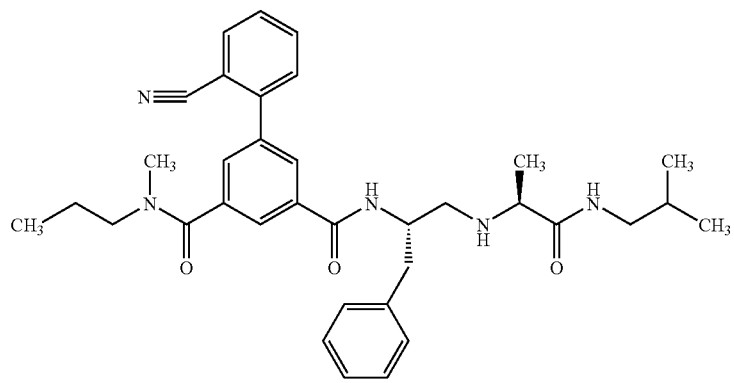
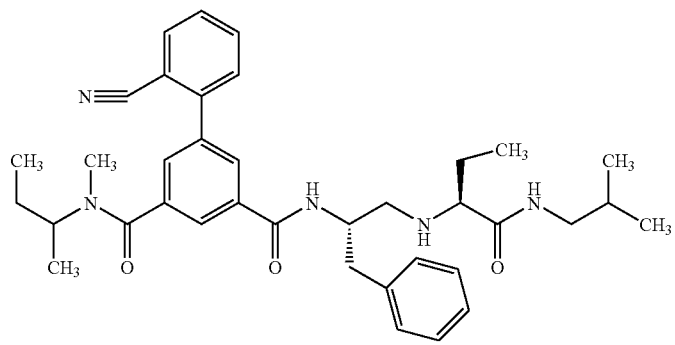

-continued
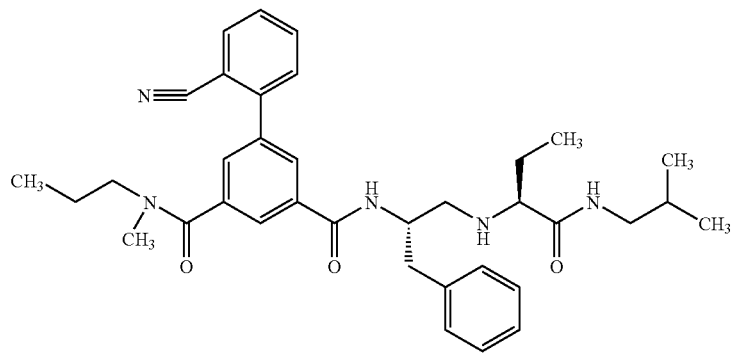
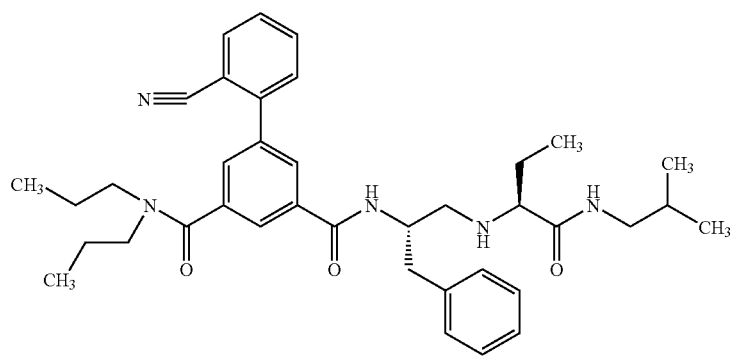
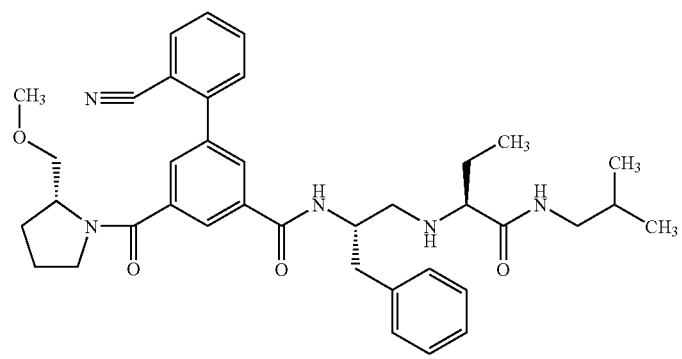
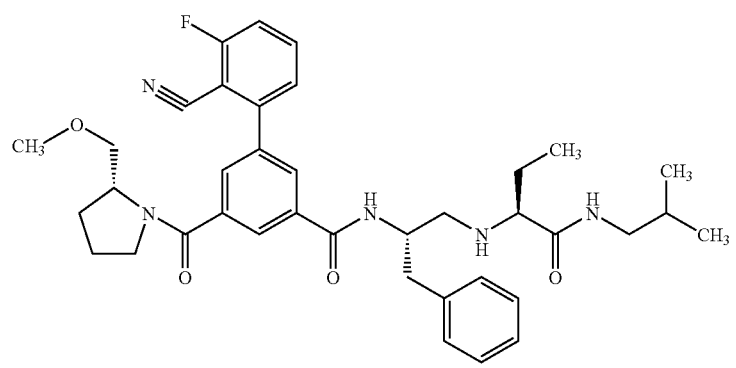

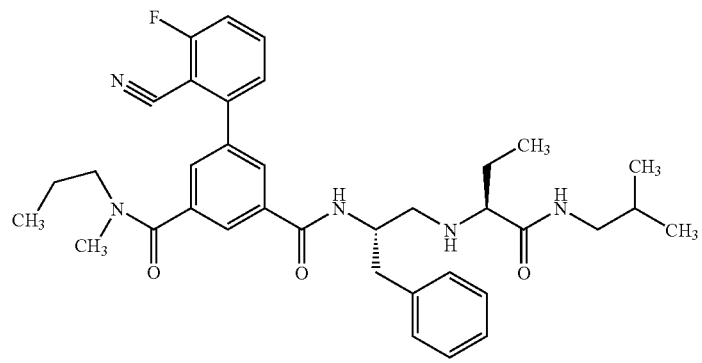
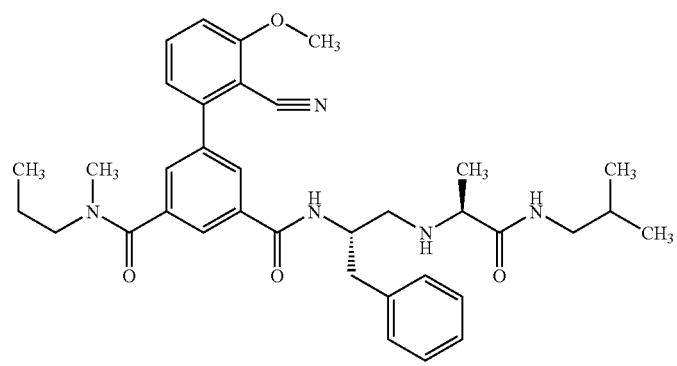
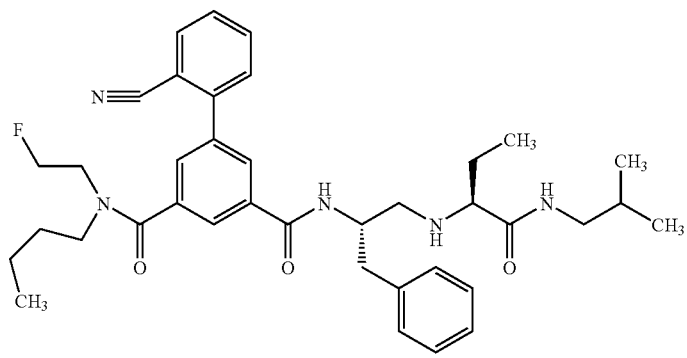
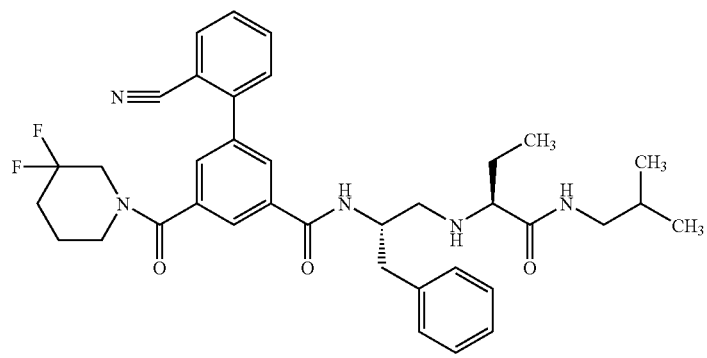

-continued
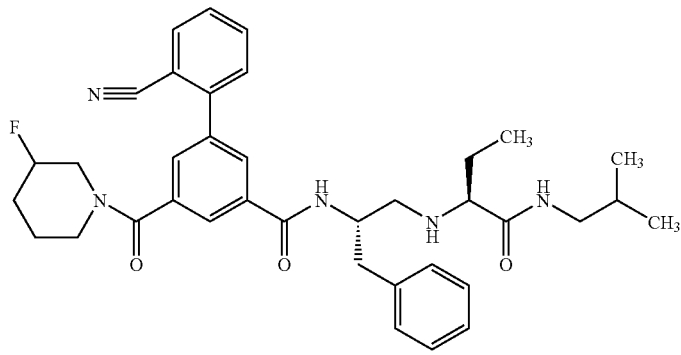
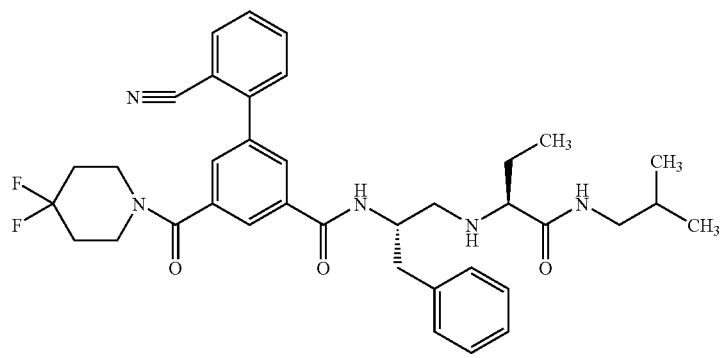
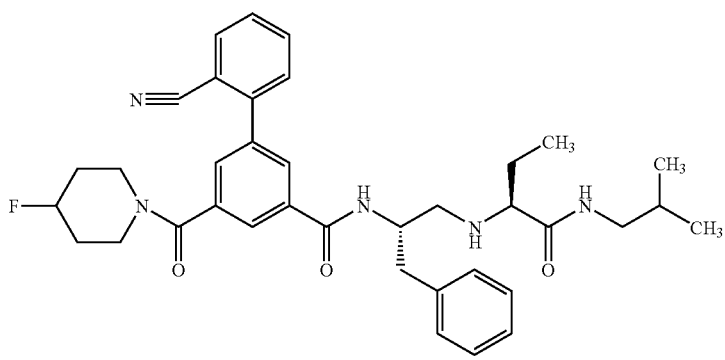
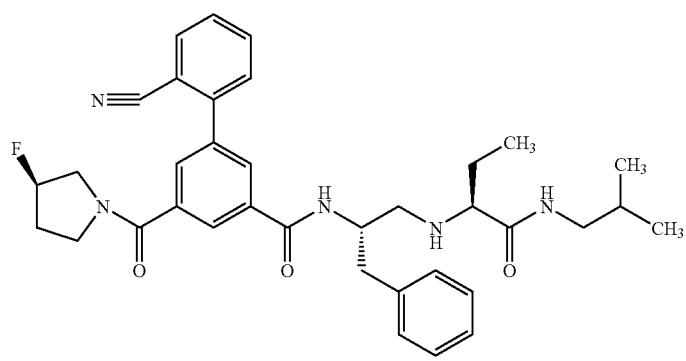

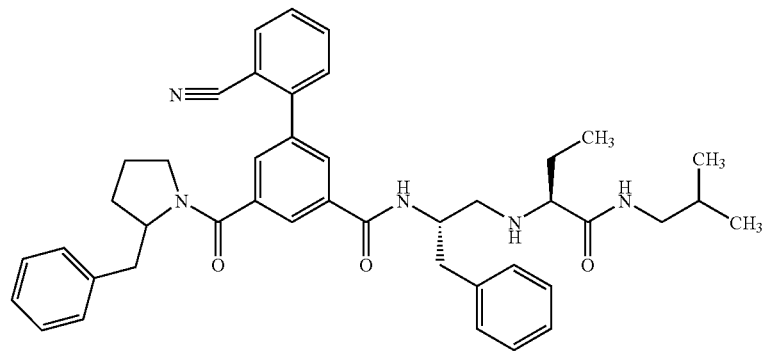
and pharmaceutically acceptable salts thereof.
12. A pharmaceutical composition comprising a therapeutically effective amount of the compound of claim 1 and a pharmaceutically acceptable carrier.
* * * * *